(12) United States Patent
Cabezas et al.

(10) Patent No.: US 7,498,147 B2
(45) Date of Patent: Mar. 3, 2009

(54) DIAGNOSIS, PREVENTION, AND/OR TREATMENT OF ATHEROSCLEROSIS AND UNDERLYING AND/OR RELATED DISEASES

(75) Inventors: Manuel Castro Cabezas, Zeist (NL); Hans van Dijk, De Bilt (NL)

(73) Assignee: Crossbeta Biosciences B.V., Utrecht (NL)

( * ) Notice: Subject to any disclaimer, the term of this patent is extended or adjusted under 35 U.S.C. 154(b) by 920 days.

(21) Appl. No.: 10/327,604

(22) Filed: Dec. 20, 2002

(65) Prior Publication Data

US 2003/0143223 A1    Jul. 31, 2003

Related U.S. Application Data

(63) Continuation-in-part of application No. PCT/NL01/00673, filed on Sep. 12, 2001.

(60) Provisional application No. 60/253,465, filed on Nov. 28, 2000.

(30) Foreign Application Priority Data

Dec. 9, 2000    (EP)    .................................. 00203156

(51) Int. Cl.
*C12Q 1/02* (2006.01)
*G01N 33/566* (2006.01)
*G01N 33/573* (2006.01)

(52) U.S. Cl. ........................... 435/29; 436/501; 436/536
(58) Field of Classification Search ........................ None
See application file for complete search history.

(56) References Cited

U.S. PATENT DOCUMENTS

| 5,833,989 A | 11/1998 | Mossakowska et al. |
| 5,859,223 A | 1/1999 | Mossakowska et al. |

FOREIGN PATENT DOCUMENTS

| WO | 94/00571 | 1/1994 |
| WO | 00/34469 | 6/2000 |
| WO | 00/35483 | 6/2000 |
| WO | 00/69894 | 11/2000 |
| WO | 00/70043 | 11/2000 |
| WO | 02/22160 | 3/2002 |
| WO | 02/22161 | 3/2002 |

OTHER PUBLICATIONS

PCT International Search Report, PCT/NL01/00673, dated Mar. 7, 2002.
Klerx et al., Microassay for Colorimetric Estimation of Complement Activity in Guinea Pig, Human and Mouse Serum, Journal of Immunological Methods, 1983, pp. 215-220; vol. 63.
Van Dijk et al., Study of the Optimal Reaction Conditions for Assay of the Mouse Alternative Complement Pathway, Journal of Immunological Methods, 1985, pp. 233-243, vol. 85.

*Primary Examiner*—David A. Saunders
*Assistant Examiner*—F. Pierre VanderVegt
(74) *Attorney, Agent, or Firm*—TraskBritt

(57) ABSTRACT

Complement is recognized as an important, humoral defense system involved in the innate (nonspecific) recognition and elimination of microbial invaders, other foreign particles or molecules, and antigen-antibody complexes from the body. The present invention makes use of the surprising notion that the handling of lipids by the body, rather than its antimicrobial activity, is the primary and most ancient function of the complement system. Consequently, atherosclerosis as observed in disorders associated with disturbed lipid metabolism (familial combined hyperlipemia (FCHL), postprandial hyperlipidemia, hypertriglyceridemia with low levels of HDL cholesterol, and insulin resistance associated with type-II diabetes and obesity), is ascribed to either genetic or acquired defects in ancient (activatory and/or regulatory) complement components. Based on this new insight, novel preventive measures and treatment modalities of disturbed lipid metabolism are introduced.

3 Claims, 11 Drawing Sheets

'Immune adherence'

'Immune adherence'

DIAGNOSIS, PREVENTION, AND/OR TREATMENT OF ATHEROSCLEROSIS AND UNDERLYING AND/OR RELATED DISEASES

CROSS-REFERENCE TO RELATED APPLICATIONS

This application is a continuation in part of PCT International Patent Application PCT/NL01/00673, filed on Sep. 12, 2001, designating the United States of America, and published, in English as WO 02/22161 A2 (Mar. 21, 2002), the contents of the entirety of which is incorporated herein by this reference. This application also claims benefit under 35 U.S.C. § 119(e) to U.S. provisional patent application No. 60/253,465 filed on Nov. 28, 2000.

TECHNICAL FIELD

The invention relates to the diagnosis, prevention, and/or treatment of atherosclerosis and/or underlying and/or associated diseases.

BACKGROUND

According to the classical view, atherosclerosis is a condition ultimately leading to the narrowing of blood vessels, impaired circulation, and restricted oxygenation of tissues (1). If this process occurs in heart vessels (coronary arteries), consequences are the clinical conditions of angina pectoris and myocardial infarction; in the brain, atherosclerosis leads to cerebrovascular accidents; in the legs, the clinical presentation is claudicatio intermittens. Classical risk factors Associated with atherosclerosis are: obesity, hypertension, smoking, diabetes, male gender, fasting hyperlipidemia, and especially increased cholesterol concentrations. Novel risk factors have emerged during the last decennia, these including hyperhomocysteinemia, hypertriglyceridemia with low HDL cholesterol concentrations, postprandial hyperlipidemia, the insulin resistance syndrome, and a positive family history for cardiovascular disease, among others.

According to epidemiological surveys, coronary heart disease (CHD) is the leading cause of death in western societies. In the United Kingdom in 1987, 31% of all deaths in males (280.177 total deaths in men) and 24% in females (total number: 286.817) were due to CHD. More than one quarter of CHD deaths in men (total CHD mortality in men: 86.978) occurred before the age of 65 years. In women (68.257 CHD deaths), the vast majority (almost 75%) occurred at ages beyond 75 years. The Dutch situation is similar and representative for other countries in Western society. In The Netherlands in 1997, there were 135.783 deaths in total (67.242 males and 68.541 females). In men, 37% of total mortality (24.664 deaths) was due to CHD and in women 38% (25.881 deaths). From 1972 to 1997, mortality due to CHD in The Netherlands decreased by 44% (age-corrected); however, hospital admissions related to CHD increased by 53%. This decrease in CHD-associated mortality is probably ascribed to improved care in coronary-care and intensive-care units. In addition, the early recognition of the above-mentioned risk factors for CHD and improved treatment of these risk factors may have led to increased survival in patients at risk.

The classical drugs for the treatment of these risk factors are cholesterol-lowering drugs (mainly statins) (3), drugs aiming at the reduction of blood pressure like angiotensin-converting-enzyme inhibitors (4) and drugs like aspirin which act on clot formation. The effects of life-style change to reduce body weight and stopping smoking have been disappointing so far, although their impact has not been established adequately on a population basis. Improvement of regulation of diabetes has resulted in decreased morbidity (less amputations, less diabetics with end-stage renal failure necessitating dialysis, and less diabetics becoming blind) (5, 6), but the incidence of cardiovascular disease in diabetics did not decrease by these measures (6, 7).

Many investigators point at the need for the recognition of concealed risk factors for CHD in diabetes (and obesity) and a more aggressive treatment of these factors should result in improved outcome. Moreover, land-mark trials with lipid-lowering drugs in secondary and primary prevention settings have resulted in significantly decreased mortality in treated patients (30% risk reduction) (2), but there were still significant numbers of patients that could not be saved by these drugs. Therefore, the identification of additional risk factors and the development of novel therapeutic interventions are expected to result in a significant reduction of total mortality due to CHD.

It has been postulated that atherosclerosis is associated with an impaired clearance of chylomicron remnants, i.e., partially hydrolyzed chylomicrons (intestinally-derived triglyceride-rich lipoproteins). Also, it was suggested (PCT International Patent Publication WO 00 34469) that clusterin could be used as a migration inhibitor of vascular smooth muscle cells in arteries whose migration and proliferation may lead to vessel injury and arterial lesion and whose migration and proliferation can be induced by atherosclerosis. Rosenberg and Silkensen (10), in reviewing the multifunctional protein role of clusterin state the determination of a common mechanism underlying its various functions would lead to a key in comprehending an important area of biology. Other researchers (11) have demonstrated that clusterin (apo J) may have a protective role against atherosclerosis as it participates in cholesterol transport.

One of the recently recognized mechanisms in the development of atherosclerosis is inflammation (8). Several studies have demonstrated that slightly elevated concentrations of C-reactive protein (CRP; a well-known acute-phase reactant named after its reactivity with the so-called C-polysaccharide of pneumococci) are predictive of coronary events in middle-aged and elderly men and women. However, the precise mechanism by which complement is involved in atherosclerosis is not known. In discussing a possible relationship between infections with pathogenic micro-organisms, MBL (an innate immune-defense plasma protein) deficiency and atherosclerosis, Madsen et al. (12) suggested the presence of unexpected non-infective mechanisms relevant to the development of atherosclerosis but could not conclusively exclude a relationship with other pathogens. The role of MBL in the immune system and the use of recombinant MBL in treating deficiencies in the immune system is well known (PCT International Patent Publication WO 00/70043). The present invention teaches how lipid metabolism, complement activation, atherogenic processes and immune responses are physiologically related.

SUMMARY OF THE INVENTION

The present inventors have elucidated a mechanism providing an explanation for the insufficient protective effects of lipid-lowering drugs, the persistently high incidence of coronary heart disease in western societies, and the relationship with markers of inflammation like CRP. As a result of this new insight, a novel approach for the diagnosis, prevention, and/or therapy of atherosclerosis and underlying or related disease(s) is presented which comprises a method for the treatment and/or prophylaxis of diseases associated with disturbances in the complement/lipid pathway by modulating the activity of one or more elements in the pathway. Such a new method may for instance be implemented at a large scale in combination with current strategies to lower mortality and morbidity by CHD.

The present invention makes use of the surprising notion that the primary and most ancient function of the complement system is the transport and targeting of lipoproteins (i.e., chylomicrons, VLDL's, LDL's, and their remnants) to the liver, rather than its antimicrobial activity. Consequently, atherosclerosis as observed in disorders associated with disturbed lipid metabolism (familial combined hyperlipemia (FCHL), postprandial hyperlipidemia, hypertriglyceridemia with low levels of HDL cholesterol, and insulin resistance associated with type-II diabetes and obesity), must be ascribed to either genetic or acquired defects in ancient (activatory and/or regulatory) complement components. Based on this new insight, novel preventive measures and treatment modalities of disturbed lipid metabolism are introduced.

In accordance with the invention, it has surprisingly been found that clearance of chylomicron remnants and in general clearance of all triglyceride-rich particles (chylomicrons, VLDL, IDL and their remnants) and LDL particles is positively regulated by the complement system; that is to say by the most ancient complement activation pathways, the "pectin" and "alternative" pathways. Delayed clearance of triglyceride-rich particles, in particular those containing apolipoprotein B as a structural protein, is related to deficiencies in the ancient complement activation pathways. Moreover, in one embodiment the invention predicts that low serum levels of the intercellular matrix proteins vitronectin and/or clusterin, which function as regulators of the "terminal" or "lytic" pathways of complement, lead to decreased intravascular integrity of chylomicron remnants. Such a decreased integrity is typically atherogenic.

Accordingly, the invention relates to the use of purified or enriched physiologic complement components, physiologic complement regulators and/or extrinsic complement modulators of natural (e.g., plant-derived), synthetic, or semi-synthetic origin in the prevention and/or treatment of atherosclerosis and underlying and/or related diseases by substituting for and/or at least diminishing deficiencies in the complement activation pathways.

Because a thorough and mechanistic insight has now been achieved, the invention provides novel diagnostic tools and formulations of specific and highly effective primary and secondary prevention strategies for disturbances leading to atherosclerosis. Dependent on what is (are) the weakest link(s) in the specific pathways of the complement system in an individual patient, a physician can, based on the considerations of the invention, modulate the activity of the complement system of the patient in order to prevent and/or treat manifestations of disease.

The present invention has as an objective to provide new and improved manners of prevention and/or treatment of atherosclerosis and underlying/related diseases. The invention further provides new and improved manners of determining the occurrence (diagnosis) of atherosclerosis and related diseases, in particular those which are associated with disturbed lipid metabolism and to classify these diseases accordingly.

A further object of the present invention is to provide for coordinated design and discovery of new drugs for the treatment of atherosclerosis and related diseases as well as providing compositions comprising modulators of the complement activation pathways which can serve as a basis or an ingredient of a pharmaceutical composition or a food product. The present invention therefore also relates to pharmaceutical products or food products that comprise such modulating compositions. As a further object, the present invention provides the use of at least one complement factor or modulator for the manufacture of a medicament for the treatment and/or prevention of atherosclerosis or an underlying and/or related disease.

In order to appreciate the importance of the invention, the inventors deem it necessary to explain the newly developed concept in much more detail. The surprisingly intricate relationship between the complement system and the clearance of chylomicron remnants unraveled by the inventors signifies a pathway not hitherto known. This unexpected finding gives rise to measures for treatment and prophylaxis of atherosclerosis that are themselves surprising, and that lead to the identification of additional risk factors and the development of novel therapeutic interventions which results in a significant reduction of total mortality due to CHD.

DETAILED DESCRIPTION OF THE INVENTION

The Complement System: General Description

The complement system (9) is a complex signaling system comprising enzymes present in blood. The complement system is involved in the early recognition and clearance of foreign bodies and antigen-antibody complexes (also called immune complexes) from the circulation and tissues. Complement is recognized as an important, humoral defense system involved in the innate (nonspecific) recognition and elimination of microbial invaders, other foreign particles or molecules, and antigen-antibody complexes from the body.

Figure 1:
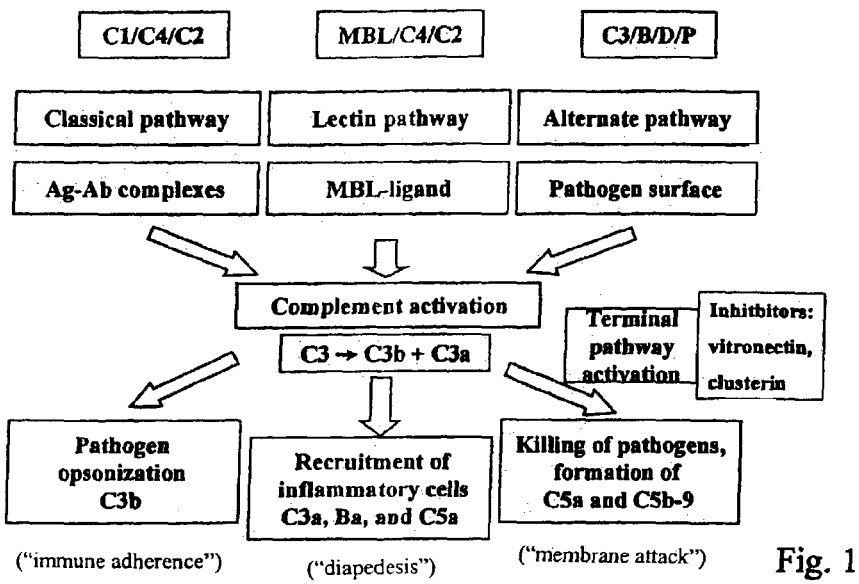
FIG. 1 shows the complement system in schematic representation.
Figure 2:
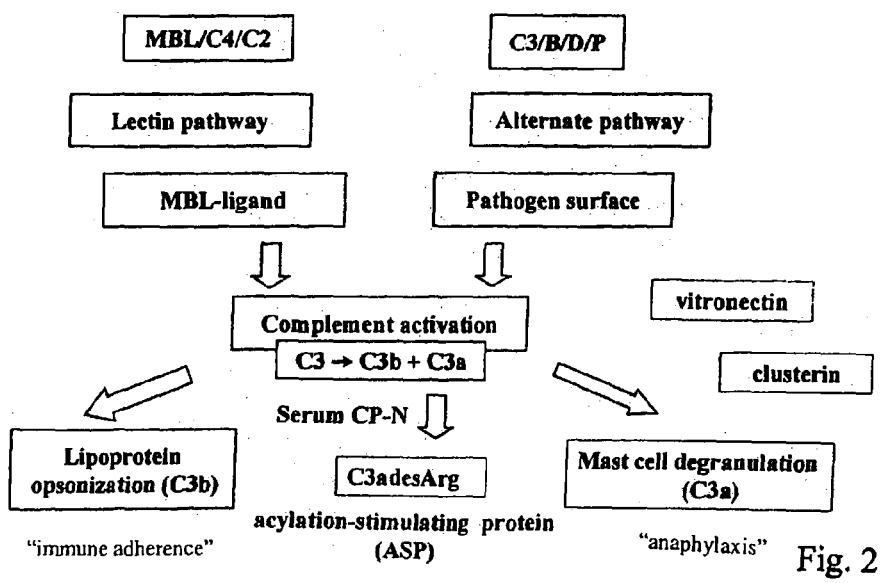
FIG. 2 shows the two most ancient pathways of the complement system in a schematic representation.

Upon the recognition of foreign material in tissue or blood, the most crucial and abundant complement component, C3, is activated by C3 convertases. This activation triggers a cascade of events that ultimately leads to the clearance of the foreign material. C3, consisting of an α chain and a β chain, is activated through a split-conversion into C3b and C3a (FIG. 1). C3a represents the N-terminus (77 amino acids) of the α chain and C3b represents the C-termini of the α and β chains. C3 convertases, of which various forms exist, can be generated through three different complement activation pathways (FIG. 1) and its synthesis is well regulated. The C3-convertase-generating pathways include, in order of descending evolutionary age, the so-called "lectin" pathway (LP), the "alternative" pathway (AP) which is also known as the "amplification loop", and the relatively young "classical" pathway (CP). During evolution, an additional system known as "terminal" or "lytic" pathway has developed on top of the complement activation system, which can destabilize membranes of, e.g., Gram-negative bacteria, virus-infected body cells, or even tumor cells by pore formation, resulting in their killing. Phylogenetic studies have pointed out that the "lectin" and "alternative" pathways are by far the most ancient complement activation pathways (about 700 million years; FIG. 2), whereas the "classical" and "lytic" pathways are relatively young (400-350 million years).

The complex nature of the complement system can be appreciated when following the fate of the split-products of C3. One of the split products, C3a, is a spasminogen and anaphylatoxin, which induces the release of histamine from basophilic cells, including tissue mast cells and basophilic granulocytes. Histamine, in turn, helps phagocytes to leave the blood vessels in order to arrive at the site of complement activation, i.e., the accumulation site of foreign material or immune complex. In blood, C3a is rapidly (in about 15 min.) inactivated by serum carboxypeptidases. The most prominent serum carboxypeptidase (sCP) in blood is the constitutively expressed sCP-N. All other sCP types are inducible and are less abundant than the N type. Upon the inactivation of C3a by carboxypeptidases, the C-terminal arginine is removed, resulting in the generation of C3adesArg. This compound is (probably identical to) an acylation-stimulating protein (ASP), a hormone that can stimulate fat accumulation in the body.

C3b and its inactivated form C3bi are opsonins, which means that they can bind covalently to sugar OH groups (via ester bonds) or protein $NH_2$ groups (via amide bonds) on material identified as "foreign." In case of such binding events, foreign material is also termed "substrate." Other complement components can also function as opsonins, among these are other C3-derivatives and the complement component C4 (see below) and derivatives thereof. Opsonins promote the clearance of foreign material by the blood-based monocytes and tissue-based macrophages, both known as mononuclear phagocytes. The mononuclear phagocytic system is present in the liver, spleen, lymph nodes, or the affected tissue itself. These specialized cells carry specific complement receptors on their surface that can bind the opsonins. Known complement receptors on phagocytes are CR1, CR3, and possibly also CR4. CR1 is an exclusive receptor of C3b whereas CR3 and CR4 are also able to bind C3bi. In contrast to mononuclear phagocytes, polymorphonuclear phagocytes (PMNs) are relatively inefficient in eliminating foreign material, at least in the absence of antibodies.

In primates, immune complexes are eliminated by the mononuclear phagocytic system in liver, spleen and bone after erythrocyte-mediated transport via the blood stream. The erythrocytes carry a restricted number of CR1 molecules on their surface to which C3b(i)-coated immune complexes can adhere. This phenomenon is called 'immune adherence'. Erythrocytes of non-primate species are CR1 negative and consequently do not mediate the transport of immune complexes to liver, spleen and bone. In primates suffering from systemic autoimmune diseases and neoplastic diseases (cancer), the clearance of immune complexes involves antibody-mediated activation of the complement system.

Microbial pathogens in the circulation are also cleared by the mononuclear phagocytic system, but only after MBL ("lectin" pathway)-mediated or antibody/C1 ("classical" pathway)-mediated activation of complement components C4, C2, and C3. This process is known to involve erythrocyte-mediated clearance as well.

The phenomenon of "immune adherence," as it has turned out, is one of importance to the present invention, as the present inventors have found that these CR1 complement receptors do not only bind immune complexes or microbial pathogens, but also chylomicrons and other triglyceride-rich particles and their remnants. Based on this finding, new methods for the treatment and prophylaxis of atherosclerosis and related disease have emerged that are based on intervention or modulation of the complement pathways involved.

As mentioned, the complement system comprises several pathways each with a multitude of protein compounds, signaling molecules, receptors, regulators and activators. To appreciate the scope of the present invention, the various pathways of complement activation will be described in some more detail.

The Complement System: the "Lectin" Pathway

Activation of the "lectin" pathway (LP) starts with the recognition and binding of foreign bodies by a serum lectin, called mannose-binding lectin (MBL). MBL is a high-molecular-weight, sugar-binding protein, present in minute amounts (about 2 μg per ml) in blood plasma. MBL and the lung surfactant proteins A (LspA) and D (LspD), belongs to the family of the collagenous lectins (collectins). C1, the first component in the "classical" pathway is a collectin-like activator of C4 and C2. Upon binding of MBL to foreign bodies, a number of MBL-associated proteins (MASPs—which are themselves esterases) become coordinately activated, ultimately leading to the generation of the active forms of the associated proteins, the LP-dependent C4, C2 and/or C3 convertases. These convertases, which have C3, C4 and C2 as their natural substrates, generate essentially five products: C3b and C3a, C4bC2a and split products C4a and C2b. Like C3b, the C4b portion of C4bC2a binds covalently to its substrate (e.g., polysaccharides or (glyco)proteins on bacteria) via ester or amide bonds, and is therefore known as an opsonin. The two split products, C4a and C2b, are released in the fluid phase. Substrate-bound C4bC2a is the LP-dependent C3 convertase, causing the conversion of C3 into C3b and C3a. Like C3a, C4a is a spasminogen and anaphylatoxin (histamine liberator), whereas C2b has kinin-like activity. Furthermore, one of the MBL-associated proteins is capable of direct activation of C3.

MBL recognizes foreign bodies by its 6 identical sugar-binding moieties with specificity for mannose, N-acetyl-glucosamine, and fucose. This makes sense, because microbial pathogens like fungi, yeasts, and, e.g., Mycobacteria carry relatively high amounts of mannose, while peptidoglycan of Gram-positive bacteria contains N-acetyl-glucosamine as one of its major building blocks.

The Complement System: The "Alternative" Pathway

Until the discovery of the "lectin" pathway in 1989, the "alternative" pathway (AP, also known as alternate pathway or alternative complement pathway), first described in 1956, was considered the most ancient complement activation route. The main function of this "alternative" pathway is to increase (amplify) the number of C3-converting sites on the substrate of complement activation: the foreign body or the immune complex. This means that, once "non-self" material has been identified by MBL and activation of the "lectin" pathway has consequently taken place, the LP-dependent C3 convertase C4bC2a present on the substrate will be amplified by AP-dependent C3 convertases in the following manner (FIG. 1): Substrate-bound C3b, generated by the LP-dependent C3 convertase C4bC2a, will bind AP component factor B which, in turn, will be activated to Bb by AP component factor D (also known as adipsin) to form the AP-dependent C3 convertase (C3bBb). Along with the formation of this new C3 convertase, the factor-B part loses a split product called Ba. The enzymic function of the AP-dependent C3 convertase is considerably stabilized upon the binding of AP component "properdin" (factor P), resulting in the AP-dependent C3 convertase complex C3bBbP. Split product Ba is a leukotaxin, which helps to direct the movement of phagocytes to the site of complement activation (primary inflammation site).

The net result of AP activation is an increase in the number of C3b and inactivated C3b (C3bi) moieties on the substrate, which promote the recognition and clearance of foreign bodies and immune complexes by, predominantly, mononuclear phagocytes (monocytes/macrophages).

The Complement System: the 'Classical' Pathway

The "classical" pathway (CP) is generally considered the youngest complement activation route, since it is dependent on antibodies (IgM and IgG), which appeared relatively late in phylogeny (from about 350 million years ago). The CP is very similar to, and therefore probably derived from the ancient "lectin" pathway, since the first CP component (C1; consisting of a complex of the collectin-like C1q and two MASP-like proteins called C1r and C1s) is both phenotypically and functionally very much related to the MBL/MASPs complex. In addition, the "classical" pathway involves "lectin" pathway complement components C4 and C2. Like the sugar-bound MBL/MASPs complex, C1 (composed of C1q, C1r, and C1s) bound to IgM- or IgG-type immune complexes becomes coordinately activated to form a C1-esterase which has C4 and C2 as its natural substrates and which gives rise to the generation of CP-dependent C3 convertases, which are identical to LP-dependent C3 convertases (substrate-bound C4bC2a complexes).

C4 exists in two isoforms known as C4A and C4B. C4A is involved in the clearance phenomenon, whereas C4B is mainly involved in the killing of bacteria and cell destruction (e.g., hemolysis). In the present description, C4 is understood to relate to the C4A isoform unless otherwise stated.

The Complement System: the Terminal or "Lytic" Pathway

When a newly formed C3b molecule does not bind to the substrate directly, but to another, substrate-bound C3 convertase (C4bC2a or C3bBbP), triple or quadruple complexes consisting of C4bC2aC3b or C3bBbC3bP are formed. These complexes have C5-converting activity indicating that they are able to split complement component C5 into C5b and C5a. This is the starting point of the so-called "terminal" or "lytic" complement pathway. Like Ba, C5a is a leukotaxin, but more potent than Ba. C5b forms a complex with C6 and C7, the resultant of which is a soluble C5b-7 complex, which has affinity for membranous bilayers. Upon insertion into a membrane of, e.g., a Gram-negative bacterium, complement component C8 will bind to the complex, which results in a new enzyme, the membrane-bound C9 polymerase (C5b-8). Under the influence of one C5b-8 complex, some 13 C9 molecules become polymerized, resulting in a cylindrical pore in the membrane that is under attack. Depending on the total number of membrane-bound poly-C9 pores, and on whether the bacterium is encapsulated or not, the Gram-negative bacterium will either be killed or be able to resist and survive membrane attack.

The Complement System: Complement Regulation and Complement Regulators

In order to prevent unwanted activation of the complement cascade, e.g., by cells of the body itself (homologous cells, in contrast to foreign or heterologous cells), complement activation on homologous cells is heavily regulated by both cell-bound complement inhibitors and regulators in the fluid phase (e.g., serum or plasma). The most important soluble regulators are:

For the "lectin" pathway:

$\alpha_2$-Macroglobulin (($\alpha$2M), serpines and C4-binding protein (C4BP), which interfere with the formation of the LP-dependent C4/C2-convertase (activated MBL/MASPs complex) and the subsequent activation of C4 and C2.

For the "alternative" pathway:

Factor H (also known as $\beta$1H) and factor H-like molecules, acting at the level of factor B binding to target-bound C3b (preventing the formation of AP-dependent C3 convertases), C3b inactivator (factor I), acting in conjunction with factor H, to convert C3b in its enzymatically inactive, but as opsonin still active form C3bi.

For the "classical" pathway:

C1INH, an inhibitor of complement component C1, acting at the level of activated C1, the C1-esterase (C1INH is also an inhibitor of other serine esterases such as kallikrein, the clotting factors XIa and XIIa, and the fibrinolysis product plasmin), and For the "lytic" pathway:

Vitronectin (S protein) and clusterin (also known as apolipoprotein J or apo J). These proteins act at the level of C5b-7 complexes, preventing their insertion into bilayer membranes and inhibiting C9 polymerization and consequently, the lysis of bacteria, viruses and body cells.

Cell-bound complement regulators include:

Complement receptor 1 (CR1) which has factor-H-like co-enzyme function versus factor I; CR1 is present on phagocytes, platelets, but also as a carrier protein on erythrocytes;

Decay-accelerating factor (DAF, which is also known as cluster of differentiation protein CD55) and membrane cofactor protein (MCP=CD46), both acting at the level of AP activation;

Homologous restriction factor with 20-k molecular mass (HRF20=CD59) and HRF60, both inhibitory at the level of C9 polymerase (C5b-8) formation; and Sialic acid, which acts similar to CD55 and CD46 at the level of the AP-dependent C3-convertase formation, but also on C9 polymerization.

The Complement System: Complement Activation and the Innate and Specific Immune System Apart from the physiological activatory and regulatory complement components mentioned above, different substances of bacterial, plant, animal, or (semi)synthetic origin are known to either activate or inhibit the complement cascade(s). These components include, i.e., bacterial lipopolysaccharides, β-glycyrrhetinic acid, phytosterols, bovine conglutinin, and polymeric substances like dextran sulphate and glucans.

Bacterial lipopolysaccharides have recently been recognized as potent activators of the "lectin" pathway. Likewise, β-glycyrrhetinic acid, as a possible activator of C4, was suggested to be able to activate the "lectin" pathway, while the phytosterols with as most important repesentatives β-sitosterol, stigmasterol, and campesterol, have been shown to activate the "alternative" pathway. Dextran sulphate functions as an acceptor site for "alternative" pathway regulatory protein factor H, and thus facilitates the "alternative" pathway-mediated activation of C3 and subsequent deposition of C3b on a substrate.

Based on their complement-activating capacity, a number of these substances, including bacterial lipopolysaccharides, dextran sulphates, and glucans, as well as lipidated muramyl-dipeptides and lipophilic quaternary ammonium compounds like dimethyldioctadecyl ammonium bromide, show potent immunological adjuvant activity, which means that they are able to stimulate antigen-specific T- and B-cell responses.

Lipid Metabolism: the Physiology of Lipid Metabolism

Under physiologic conditions, about 90% of the ingested fat (triglycerides) is taken up by the epithelial cells of the small intestine, resulting in the generation of intestinally-derived triglyceride-rich lipoproteins, called chylomicrons. These chylomicrons are transcytosed through the epithelial cells and delivered at their basolateral side to the sub-epithelial interstitium. The structure of chylomicrons is stabilized by a large, highly glycosylated protein, called apolipoprotein B48 (apo B48), of which the most dominant glucoses residues are: mannose (17.8%), N-acetyl-glucosamine (16.8%), galactose (13.4%), and fucose (3.4%) which, in fact, fully matches with the binding specificities of MBL. Apo B48 is the 5' splice product of a larger apob gene which—in human intestinal epithelial cells—is posttranscriptionally modified by a unique editing enzyme. This modification results in a premature stop codon leading to the translation of only 48% of the apob mRNA. Since the human liver lacks the unique editing enzyme, apob transcription in the liver results in the synthesis of full-length apo B100. This protein is the structural protein of the liver-derived triglyceride-rich particles known as VLDL (very low density lipoproteins) and their remnants (IDL's and LDL's).

From the sub-epithelial interstitium, chylomicrons are collected in tissue fluid (lymph). Via lymph vessels, they are transported to subsequent draining lymph nodes and, through the thoracic duct and the left subclavian vein, they finally arrive in the blood stream. Once in the circulation, chylomicrons are rapidly converted into chylomicron remnants by the action of vascular-endothelium-associated lipoprotein lipase (LPL). Chylomicron remnants are present in blood in different sizes.

Chylomicrons and chylomicron remnants are subsequently cleared efficiently by the liver from where they can undergo bile-mediated excretion via the stools. However, the efficiency of the process of chylomicron and chylomicron-remnant targeting to the liver is far from understood, while the subsequent hepatic clearance of these triglyceride-rich particles has not completely been elucidated either. In the liver, it involves at least the activity of the hepatic triglyceride lipase (HTGL), interaction with specific apo E receptors, and non-receptor binding to the cellular surface in the hepatic space of Disse. Several local receptors may be involved including low-density-lipoprotein receptor-related protein/$\alpha_2$-Macroglobulin receptor (LRP-$\alpha_2$M), a parenchymal liver cell "chylomicron remnant receptor," the asialoglycoprotein receptor, the lipolysis-stimulated receptor, and the LDL (low density lipoprotein) receptor. Recently, the VLDL receptor, a new member of the LDL receptor supergene family, which is not present in the liver, has been recognized as a physiological receptor for chylomicron remnants.

Cholesterol, delivered to the liver by chylomicrons and chylomicron remnants, is largely re-secreted into the circulation after incorporation into very-low density lipoproteins (VLDL). This cholesterol is further employed by the adrenals and genitals as a skeleton for their steroid-hormone synthesis.

Figure 3:
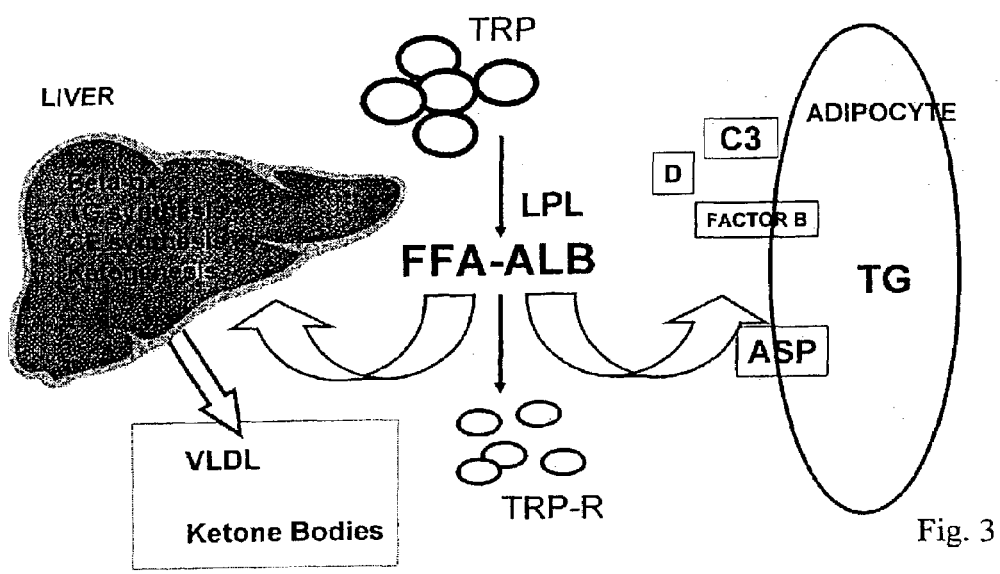
FIG. 3 shows the relationship between triglyceride rich particles (TRP), their remnants (TRP-R), the position of lipoprotein lipase (LPL), free fatty-acids (FFA), acylation-stimulating protein (ASP), several complement components (C3, factor B and factor D) in relation to triglyceride (TG) uptake by adipocytes and liver-derived very low density lipoproteins (VLDL).

Free fatty acids (FFA) arising from the breakdown of chylomicrons by the endothelial LPL are transported over the mucosa towards sub-endothelial fat cells (adipocytes) in which they become re-esterified into intracellular triglycerides (FIG. 3). The uptake and incorporation of FFA into adipocytes is under the positive control of a hormone called acylation-stimulating protein (ASP).

Similarly to the hydrolysis of triglycerides in chylomicrons, VLDL may become VLDL remnants also called IDL (intermediate-density lipoproteins) by the lipolytic action of LPL, in this case under the positive and negative control of two other apolipoproteins, apo CII and apo CIII (11), respectively. IDL are rich in apo E which functions as the ligand for the hepatic LDL receptor and "remnant-receptor" (=LRP, LDL-receptor-related protein, a member of the LDL-receptor family comprising complement repeats; possibly older than the LDL-receptor itself). Apo E (formerly "Arginine Rich Apoprotein") is one of the protein constituents of triglyceride-rich lipoproteins. Chylomicron remnants depend on apo E for their binding to the receptors, since the apo B48 structural protein does not contain the (carboxy-terminal) binding site for the LDL-receptor and 'remnant receptor'. Apo E is synthesized by almost all tissues but not by the epithelium of the intestine. The major organ responsible for apo E synthesis is the liver. As a result, chylomicrons receive apo E from HDL in the circulation, and therefore apo E is an exchangeable apoprotein. In the liver-sinusoids, hepatocytes secrete apo E resulting in an enrichment of remnant particles, thereby facilitating their removal from the circulation. There are 3 major apo E isoforms which are genetically determined: Apo E3 (the most common), apo E2 (which results in a minority of the cases in dysbetalipoproteinemia in homozygotes), and apo E4. The latter has the highest affinity for binding to the receptors, while apo E2 exhibits the lowest affinity. Apo E4-individuals are highly responsive to dietary changes and cholesterol and fat enriched diets lead to higher plasma cholesterol concentrations in these individuals, due to down-regulation of LDL-receptors.

Under physiological conditions, IDL are taken up by LDL-receptors in the liver, by which organ the lipoproteins are degraded and cholesterol is removed from the body by excretion into the bile.

Although much is known, the metabolic pathways of the intestinally- and liver-derived triglyceride-rich particles in blood, chylomicrons and VLDL, respectively, and their remnants have hitherto only partially been identified. It has been shown that these pathways comprise common elements and show a certain overlap. However, until the present invention, the very efficient targeting to the liver of chylomicrons and chylomicron remnants under physiological conditions and their clearance was far from understood.

Lipid Metabolism: Aberrant Lipid and/or Free-Fatty-Acid Metabolism

Chylomicron remnants are potentially atherogenic (atherosclerosis generating) particles due to their ability to directly induce foam-cell formation, without any modification. Low-density lipoprotein particles (LDL), in contrast, must be oxidized before they induce transformation of mononuclear phagocytes into foam cells. Mononuclear phagocytes have an LDL receptor by which they are able to bind, take up, internalize and subsequently degrade native LDL. As soon as the intracellular free cholesterol levels reach a threshold value the LDL receptors are down-regulated and the internalization process is stopped. Oxidized LDL particles, on the other hand, are taken up by 'scavenger' receptors, which are not down-regulated by cholesterol.

Since chylomicrons, VLDL, and their remnants compete for the same metabolic pathways, patients with delayed remnant clearance may experience a temporary accumulation of chylomicrons and chylomicron remnants in the circulation, which obviously contributes to the process of atherogenesis. Such situations are likely to occur in patients with familial combined hyperlipidemia (FCHL), type-2 diabetes mellitus, insulin resistance, and obesity. Enhanced plasma VLDL levels in these situations are associated with delayed clearance of chylomicron remnants.

Similar mechanisms are involved in conditions in which the clearance of remnant particles is impaired due to mutations in the apo E ligand gene (type III hyperlipidemia=familial dysbetalipoproteinemia), the LDL receptor (familial hypercholesterolemia; FH), familial defective apo B100 (FDB) and after menopause. In these conditions, which are all associated with the development of (premature) atherosclerosis, a delayed clearance of chylomicron remnants has been established due to an impaired binding to receptors in the liver. Other disorders associated with impaired remnant clearance are apo CII deficiency, (partial) lipoprotein lipase (LPL) deficiency, and hepatic triglyceride lipase (HTGL) deficiency. In these disorders, the conversion of triglyceride-rich particles into their remnants is delayed, leading to an accumulation in the circulation of triglyceride-rich particles of different sizes and triglyceride content.

In many endocrinological disorders like hypothyroidism, growth hormone deficiency, hypercortisolism by endogenous or exogenous corticosteroids, and the postmenopausal state, a decreased clearance of chylomicron remnants has been established when compared with the control situation. Finally, in patients with premature atherosclerosis and normal fasting plasma lipids (40% of all patients with myocardial infarction below 60 years of age in males and beyond 65 years of age in females), chylomicron-remnant clearance is decreased. It has been hypothesized and it is widely accepted that this may be one of the important mechanisms underlying atherosclerosis in these groups of patients. Identification of the underlying defect(s) in these patients and modulation and improvement of their chylomicron-remnant clearance will contribute to a reduction of the risk for coronary artery disease and therefore to decreased morbidity and mortality.

Free fatty acids (FFA) arising from the breakdown of chylomicrons by the endothelial lipoprotein lipase (LPL) and their uptake by the adipocytes stimulate these adipocytes to synthesize complement component C3 and "alternative" pathway components factors B and D (note that in healthy individuals, there is a linear relationship between total body fat and C3 levels), and according to the invention complement activation occurs.

The prior art discloses several important pathways involved in lipid metabolism and remnant clearance. However, designing optimal treatment and/or prophylactic measures for atherosclerosis and underlying and/or related diseases have thus far been impossible to achieve. It is now found by the present inventors that the existence of a pathway that was hitherto unknown allows for the first time the development of such measures based on a more complete and physiological and immunological understanding of the diseases. The surprisingly intricate relationship between the complement system and the clearance of chylomicron remnants unraveled by the inventors signifies the presence of such a pathway, which is termed the lipid eliminating complement activation pathway or complement/lipid pathway.

Due to this new finding the identification of additional risk factors, novel therapeutic interventions and pharmaceuticals and the treatment and prophylaxis of atherosclerosis have now become available, which will result in a significant reduction in occurrence and/or progression of this disease and other diseases associated with this pathway. The novel pathway was revealed inter alia by three independent findings. The first finding comprises that chylomicrons can induce complement activation. The second finding comprises that chylomicrons bind to erythrocytes which binding comprises complement factors as a result of which lipid transport through the blood is complement and erythrocyte mediated. The third finding relates to the glycosylation of apolipoprotein B, its kinship to MBL binding specificity and the insight that the complement-mediated lipid transport may thus be modulated through intervention in the complement/lipid pathway and its individual elements or components. Such elements or components are understood to comprise all molecules and complex substances that play a role in the complement/lipid pathway.

Figure 4A:
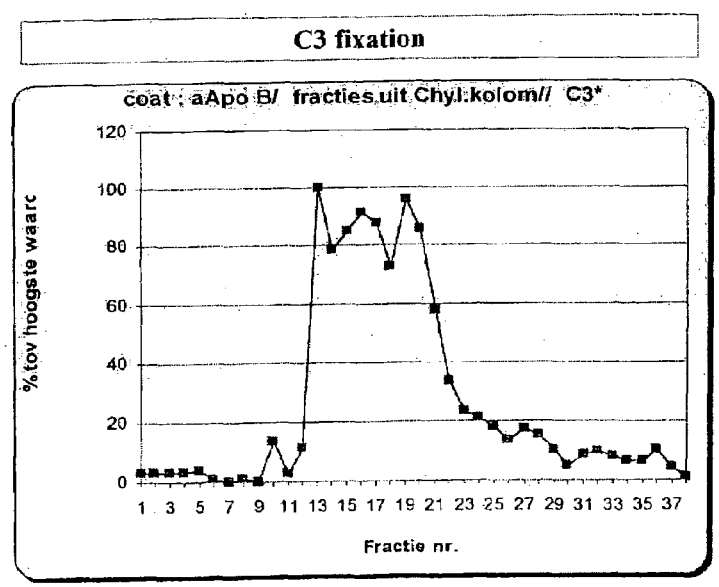
FIGS. 4A to E show the binding to chylomicrons of C3, MBL, clusterin and vitronectin as determined in example 1.
Figure 4B:
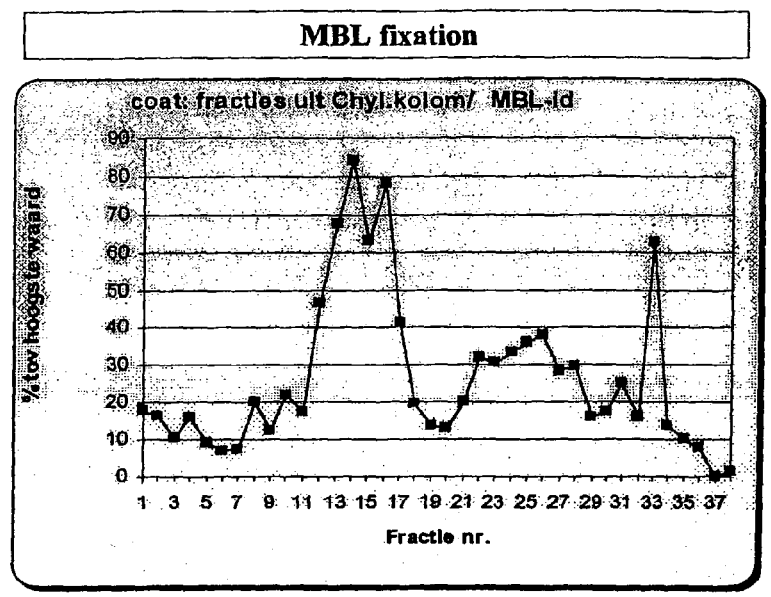
Figure 4C:
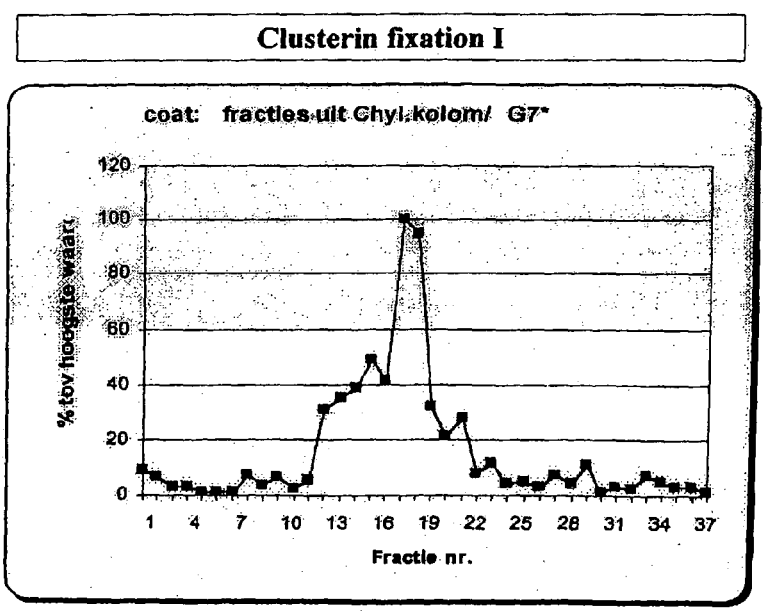
Figure 4D:
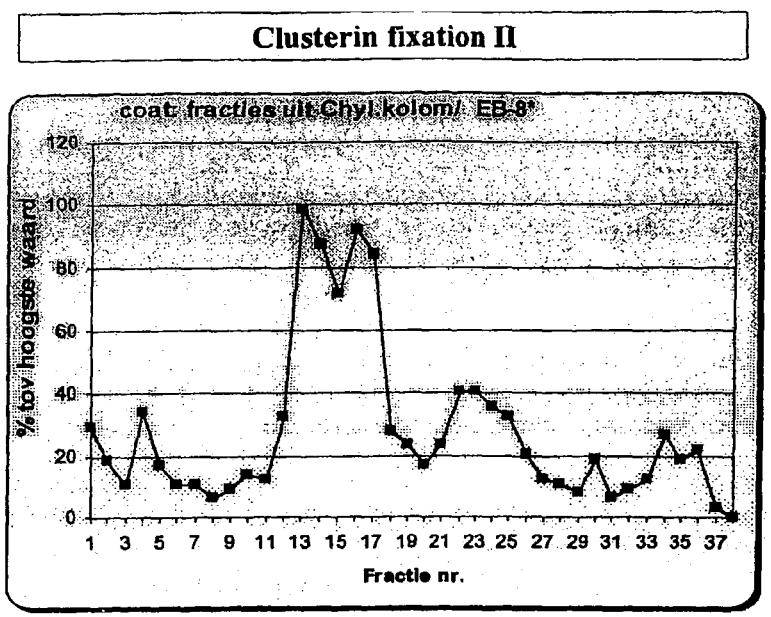
Figure 4E:
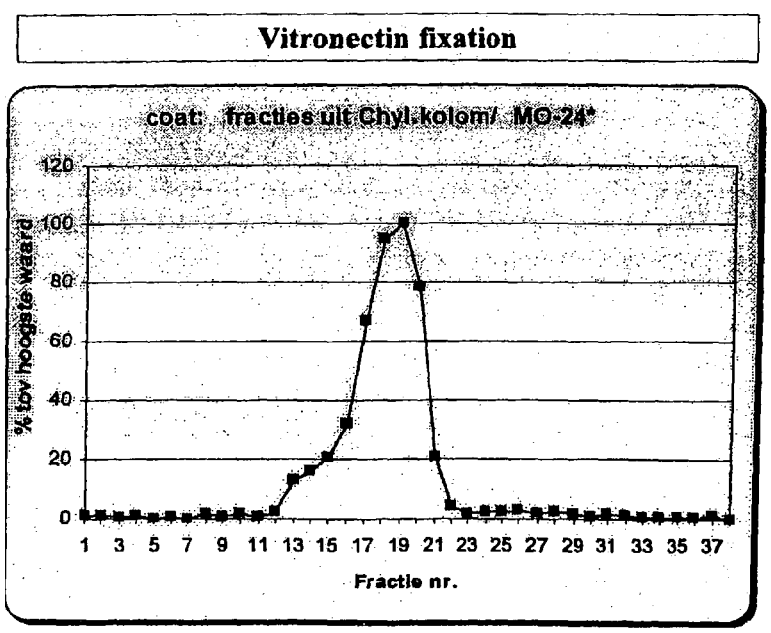

It has now surprisingly been found that chylomicrons, isolated from healthy individuals after an oral fat load, carry complement components C3 (i.e., the opsonins C3b and/or C3bi) (FIG. 4A). Thus, these chylomicrons initiate complement activation. In addition, it was also surprisingly found that chylomicrons, isolated from healthy individuals after an oral fat load, also carry the "lectin" pathway complement component mannose-binding lectin (MBL), and the terminal-complement-pathway inhibitors clusterin and vitronectin (FIGS. 4B-E). Thus, chylomicrons activate the "lectin" pathway (MBL-binding) which may ultimately lead to opsonization with C3b(i) (see "lectin" pathway)) and to binding to the CR1 receptor of phagocytes and erythrocytes (see general description of complement system). Furthermore, the presence of clusterin and vitronectin indicates a capacity to inhibit the "terminal" pathway of the human complement system.

Figure 5A:
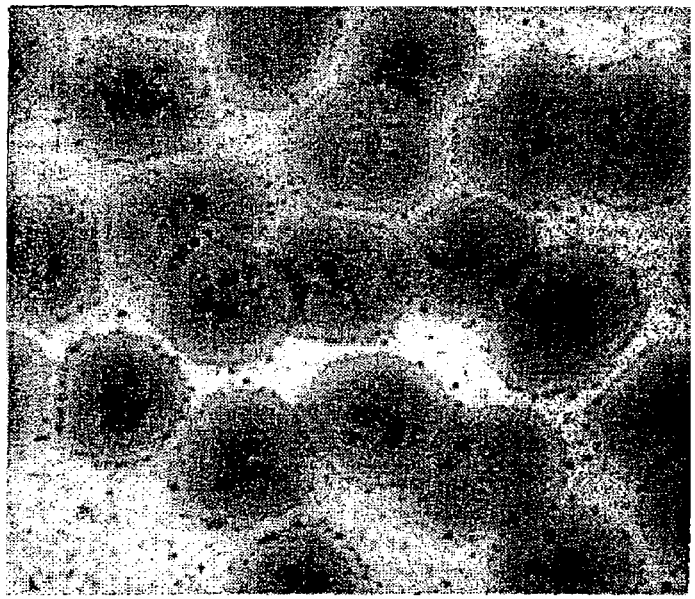
FIGS. 5A and B show the effect of immune adherence of triglyceride-rich particles to erythrocytes in blood after staining with Sudan Black as determined in example 2.
Figure 5B:
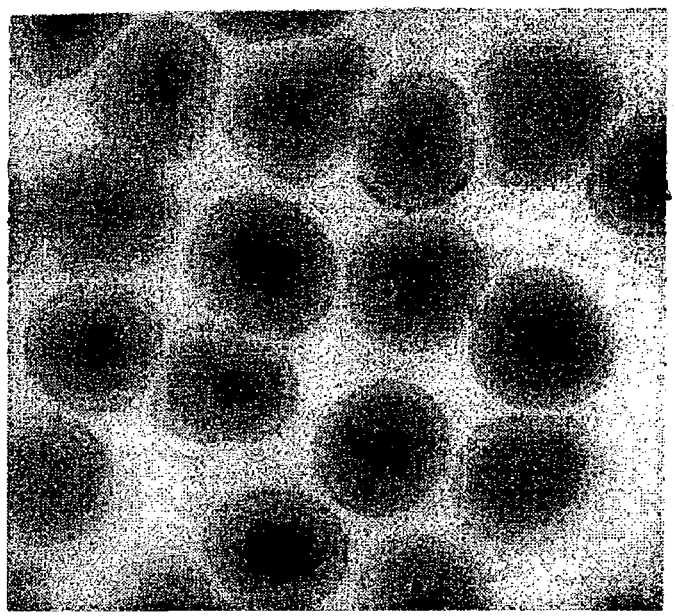

It was indeed found that virtually all erythrocytes of healthy volunteers carry chylomicrons and chylomicron remnants (FIG. 5A), whereas erythrocytes in the 'fasting' state carry considerably less chylomicrons and chylomicron remnants (FIG. 5B). This finding is in accordance with the new concept of an erythrocyte-mediated elimination of triglyceride-rich particles (and possibly also LDL particles) and complement-mediated lipid transport, and can be interpreted in terms of immune adherence of remnant particles and targeting of lipids to the liver and spleen.

The pathway revealed by the present inventors provides an explanation for the observed complement activation and for a more complete physiological and immunological understanding of atherosclerosis and/or underlying and/or related disease. The present inventors disclose that the prominent glycosylation sites of apolipoproteins B48 and B100, that are present as structural proteins on plasma chylomicrons and VLDL, respectively, match fully with the mannose, N-acetyl-glucosamine, and/or fucose binding specificity of MBL. This means that triglyceride-rich particles (LDL, chylomicrons, VLDL, etc.) in blood directly activate the complement system's "lectin" pathway through binding of apolipoprotein B to MBL.

As an intrinsic complement activator (of MBL), apo B is potentially very harmful (note the existence of autoantibodies against the C3 convertases F-42 and C3 nephritic factor in patients with collagen diseases). In particular, the intrinsic complement activatory nature of the structural apolipoprotein B molecules of triglyceride-rich particles is now predicted to be harmful for individuals with decreased serum levels of "terminal" pathway inhibitors vitronectin and/or clusterin, since such a situation will, subsequent to "lectin" pathway activation, allow "terminal" pathway activation to occur. "Terminal" pathway activation on triglyceride-rich particles may result in the release of atherogenic lipid material, particularly in patients with a genetic or acquired deficiency in the "terminal" pathway regulators vitronectin or clusterin. The binding of the "terminal" pathway inhibitors vitronectin and clusterin to chylomicrons can teleologically be explained in terms of protection from atherosclerosis.

Combination of chylomicron (remnant)-induced complement activation of the "lectin" pathway, the matching of glycosylation sites of apolipoproteins B48 and B100, and the erythrocyte-mediated elimination of triglyceride-rich particles predicts that increased levels of triglyceride-rich particles in blood, as occurring in FCHL and other disorders associated with atherogenic disturbances of lipid metabolism, is due to sub optimal erythrocyte-dependent clearance of chylomicrons and/or VLDL.

Also, disturbances in chylomicron- and/or VLDL- and/or chylomicron-remnant- and/or VLDL-remnant-mediated complement activation will lead to impaired lipid metabolism. Likewise, disturbances in the complement cascade, albeit subtle and, e.g., acquired, may also lead to impaired lipid metabolism and, in the long term, to atherosclerosis and CHD.

This bears considerable consequences for the treatment and prophylaxis of all diseases related to the complement/lipid pathway, specifically those relating to disturbances in lipid metabolism. Such diseases are recognized to comprise atherosclerosis and underlying or related disorders which include, but are not limited to, ischemia, hyperlipidemia, such as familial combined hyperlipemia (FCHL), postprandial hyperlipidemia and hypertriglyceridemia with low levels of HDL cholesterol, insulin resistance associated with type-II diabetes, obesity, coronary heart disease and premature atherosclerosis.

Other diseases related to the disturbances in the complement/lipid pathway are more immunological in appearance. The similarity in their elimination pathways predicts that triglyceride-rich particles have to compete with soluble immune complexes and/or microbes for elimination sites on erythrocytes and in the liver and spleen, which would explain the disturbed lipid metabolism in, e.g., septic shock. This bears considerable consequences for the treatment and prophylaxis of diseases such as, but not limited to, the auto-immune disorders systemic lupus erythematosus (SLE), rheumatoid arthritis (RA) and paroxysmal nocturnal hemoglobinuria (PNH), virtually all infectious diseases and related disorders such as AIDS-related (secondary) lipodystrophy, septic shock, and multiple organ failure, inflammatory diseases such as Crohn's disease, inflammatory bowel syndrome (IBS), thermal injury including burns and frostbite, uveitis, psoriasis, asthma and neoplastic diseases such as cancer. This immunological aspect of the present invention holds consequences for improving the effectiveness of vaccination programs.

Disorders directly related to the complement/lipid pathway comprise
  disturbances in chylomicron-, chylomicron-remnant, VLDL- and/or VLDL-remnant-mediated complement activation,
  disturbances in the complement cascade itself,
  disturbances in erythrocyte-dependent chylomicron remnant and/or VLDL-remnant clearance,
  disturbances in the complement-mediated lipid metabolism,
  disturbances in the regulation of lipid metabolism.

Such disorders are atherogenic and may lead to atherosclerosis and/or an underlying and/or related disease or to a disease directly related to disturbed lipid metabolism or to a disease which may seem to be more related to an immunological disorder or malfunction such as auto-immune diseases, infectious diseases, neoplastic diseases and/or inflammatory diseases.

Treatment and/or prophylaxis can as a benefit of the present invention occur by correction of disturbed complement function, in case of impaired complement-mediated lipid metabolism and will lead to an amelioration of lipid metabolism. By correcting the disturbed complement function, in case of impaired complement-mediated lipid metabolism, an amelioration of disorders associated with impaired or disturbed chylomicron remnant clearance is achieved.

Further, correction of disturbed complement function, in case of impaired complement-mediated lipid metabolism, will result in an amelioration of atherosclerosis and underlying or otherwise related diseases such as FCHL, insulin resistance in association with type-2 diabetes and/or obesity, or coronary heart disease/premature atherosclerosis.

Further, correction of disturbed complement function, in case of impaired complement-mediated lipid metabolism, will result in an amelioration of diseases of the immune system, as well as concomitant infectious, autoimmune, neoplastic or hematological diseases related to impaired complement-dependent lipid metabolism.

Disturbances of lipid metabolism due to delayed or disturbed erythrocyte-dependent clearance of chylomicrons and/or VLDL may have a number of possible causes, which will determine the nature of the corrective measure. There may be
  i) congenital defects in glycosylation of apo B48 and/or apo B100; or
  ii) absolute (homozygous), or relative or acquired deficiencies of individual complement components of the "lectin" and "alternative" pathways (such deficiencies are known to occur for MBL (9% of the population), C4A (defective gene frequency 10-13% the population), C4B (defective gene frequency 7-18% of the population), C2 (rare), C3 (rare), factor B (rare) and factor D (rare)); or
  iii) deficiencies of serum carboxypeptidases (sCP) which exclude the conversion of C3a into C3adesArg (incidence unknown); or
  iv) absolute (rare) or relative (quite common) deficiencies of complement receptor 1 (CR1) on erythrocytes as occurring in some patients with systemic lupus erythematosus (SLE);
  v) deficiencies of terminal-pathway regulator vitronectin (4% of the population), which may lead to the lysis of triglyceride-rich particles resulting in unwanted deposition of lipids; or
  vi) decreased serum levels of clusterin in association with exacerbations of SLE or with circulating immune complexes accompanying neoplastic diseases (deficiencies of clusterin are rare; <<1% of the population).

The incidence of serious cardiovascular disease (37% in 1997) in the Netherlands expressed as percentage of total numbers of fatal cases per year, matches well with the combined figures for MBL, C4A, C4B, vitronectin, and clusterin deficiencies, corrected for the incidence of double and triple deficiencies.

It is one embodiment of the present invention to provide a method for the treatment and/or prophylaxis of diseases associated with disturbances in the complement/lipid pathway by modulating the activity of one or more elements in the pathway.

In another embodiment according to the invention the activity of one or more elements of the lectin pathway and/or the alternative pathway of complement activation are modulated.

Modulating according to the present invention should be understood as regulating, controlling, blocking, inhibiting, stimulating, activating, mimicking, bypassing, correcting, removing, washing, administering, adding, and/or substituting one or more elements in the pathway or, in more general terms, intervening in the pathway.

In one aspect of the invention, the elements in this pathway comprise triglyceride-rich particles and/or their remnants and their constitutive proteins, complement proteins, complement activators, complement inhibitors, complement regulators and/or complement receptors.

In one embodiment, the activity of one or more elements is modulated through administration of a modulator.

Modulators according to the invention are substances that can bring about a modulation in the complement/lipid pathway or the complement system and may comprise triglyceride-rich particles and/or remnants thereof and/or constitutive proteins thereof, complement proteins, complement activators, complement inhibitors such as serpines, factor H, factor I and/or C1INH, complement regulators such as $\alpha$2M, their metabolic precursors, encoding genes and/or fragments thereof and they may be of physiologic (human or primate-derived), natural (e.g., plant-derived), recombinant, synthetic and/or semi-synthetic origin in enriched, purified and/or chemically modified, complete and/or partial form, as metabolic precursor, as biochemically functional analogue or as functional equivalent of a (physiologic) modulator and/or derivatives thereof used alone or in combination.

"Functional equivalents" as used herein are understood to comprise molecules having at least one function of the original compound, preferably all functions of the original compound (although not necessarily to the same extent), more preferably chemically similar compounds, most preferably compounds differing by at most three groups not relevant for the relevant activity and/or function of the original compound. In the context of the present invention, functional equivalents of complement factors are understood to comprise the split products of these factors.

In a preferred embodiment, modulators may be MBL-replacement factors, which exhibit one or more functions of the mannose binding lectin such as binding to C3b or a mimetic thereof, and/or binding to the prominent apo B glycosylation sites or mimetics thereof. Such an MBL-replacement factor may comprise lectins derived from plants such as, e.g., concanavalin A, peanut lectin, phytohemagglutinin or wheat-germ agglutinin, but they may also comprise purified or enriched physiologic MBL or synthetic, or semi-synthetic mimetics of MBL and/or functional equivalents of MBL and may be used in an aspect of the invention relating to substituting for MBL deficiencies in the complement/lipid pathway. MBL replacement compounds also comprise lipid-C3 conjugates, In another preferred embodiment, modulators may comprise apo B-replacement factors, which may be functional equivalents of apo B that, e.g., exhibit one or more functions of apolipoprotein B48 or B100 such as binding to MBL or mimetics thereof and an ability to form a constituent of a lipoprotein or a mimetic thereof. Such an apo B-replacement factor may be chosen from the group comprising physiologic apo B48 or B100, natural lipo-oligosaccharides, lipopolysaccharides, lipidated oligo- or polysaccharides, glycoproteins, $\beta$-glycyrrhetinic acid, chylomicron-bound sialic acid, phytosterols ($\beta$-sitosterol, campesterol, and/or stigmasterol) and (an)other amphiphilic (=partially hydrophobic and partially hydrophilic) complement activator(s) (e.g., mannosylated, N-acetylglucosaminylated, and/or fucosylated phytosterols, or mannosylated, N-acetylglucosaminylated, and/or fucosylated membrane lipids, such as phosphoglycerides, glycolipids such as cerebroside or ganglioside, or sphingomyelin, phosphatidyl choline, phosphatidyl serine, phosphatidyl ethanolamine, phosphatidyl inositol, diphosphatidyl glycerol or sphingosine), stanols (glycosylated and non-glycosylated), lipidated dextran sulphate(s), (lipo)glucan(s), lipidated tertiary or quaternary ammonium compounds, sialylated glycolipids, combinations thereof and single and/or combined related substances. In general, suitable apo B-replacement factors comprise amphiphilic compounds or derivatives thereof wherein the hydrophilic part comprises one or more cationic, anionic and/or polar groups and wherein the hydrophobic part comprises one or more fatty-acid ester moieties. The fatty-acid ester moieties may comprise carbon chain lengths from 1 to 50 carbon atoms, they may be straight and/or branched and they may comprise saturated and/or unsaturated fatty acids.

Preferred amphiphilic modulators additionally comprise one or more sugar moieties, such as N-acetylgalactosamine, galactose and/or sialic acid, which allow interaction with a lectin binding site. In a most preferred embodiment according to the invention, such one or more sugar moieties are mannose, N-acetylglucosamine, and/or fucose moieties that allow interaction with the lectin binding site of MBL. Other suitable apo B replacement factors may comprise an IgA or IgD antibody, which is heavily mannosylated, N-acetylglucosaminylated, and/or fucosylated of either polyclonal or humanized monoclonal or combinatorial origin, directed towards one of the apolipoproteins of chylomicrons or very low-density lipoproteins (VLDL). Such antibodies may also be bi-specific antibodies reactive towards both apoB and CR1, thereby being able to, e.g., create bonds between its two antigens.

In another embodiment, modulators may be selected from the group comprising MBL and MBL-replacement factors, C4A and functional equivalents thereof, C4B and functional equivalents thereof, C2 and functional equivalents thereof, C3 and functional equivalents thereof, IgG- and IgM-antibodies raised against triglyceride-rich particles and LDL or parts thereof, C3adesArg, factor B and functional equivalents thereof, factor D and functional equivalents thereof, factor P and functional equivalents thereof, serum carboxypeptidases such as sCP-N and functional equivalents thereof, erythrocyte-bound CR1 and functional equivalents thereof, free CR1 and functional equivalents thereof, CR1 mimetics such as C3b antibodies, vitronectin and functional equivalents thereof, clusterin and functional equivalents thereof and apo B (48 and 100) and apo B replacement factors and esterases such as one of the MASP-proteins and functional equivalents thereof.

In another preferred embodiment, modulators comprise antibodies. In a more preferred embodiment, these antibodies for the classical pathway are IgG and/or IgM antibodies.

In another embodiment, the group comprising apo B replacement factors also comprises an IgA or IgD antibody directed against an apo B lipoprotein, which antibody is heavily mannosylated, and/or heavily N-acetylglucosaminylated and/or heavily fucosylated.

In a more preferred embodiment, the modulator for the classical pathway is selected from the group of antibodies wherein the antibody comprises a polyclonal and/or humanized monoclonal and/or combinatorial antibody and/or bispecific antibodies reactive towards both an apo B and CR1.

Administration of a modulator may comprise oral administration, nasal administration, pulmonary administration, inhalation, anal and/or rectal administration, intravenous injection, intramuscular injection, intradermal injection, subcutaneous injection, mucous membrane diffusion, skin absorption, topical application, extracorporeal circulation-mediated administration and/or any other suitable administration route, single or in combination.

Modulators may be administered in pure form and/or diluted form, they may be in solid, semi-solid, crystalline and/or fluidic form, dissolved and/or dispersed single or as a constituent of a fluid, a spray, a gel, an ointment, a tablet, a suppository, a capsule (synthetic, natural or viral), a powder, a(n) (clinical) intralipid, a (clinical) food product, a (clinical) food additive, a lipidated vaccine for oral application, slow-release and/or direct release carrier that contains the modulator and/or any other suitable formulation for administration. Furthermore, modulators may be unlabeled or labeled with signal molecules or groups such as, e.g., dyes, fluorochromes, radioactive atoms or groups, enzymes or luminescent molecules or groups.

Apo B replacement factors according to the invention may be administered alone or in combination with other modulators in a natural, artificial or synthetic lipid carrier compound comprising lipoproteins, lipid micelles, lipid vesicles, artificial lipid bilayer membranes, chylomicrons, liposomes and/or other suitable and/or pharmaceutically accepted lipid substance. Clinical intralipids (fat emulsions) used in relation to the invention as parenteral feeding may comprise such a lipid carrier compound in combination with one or more modulators. In a preferred embodiment of such a parenteral feeding, the lipid carrier is selected from the group comprising mineral oil and natural oils, such as soy oil, sunflower oil, peanut oil, olive oil, palm oil and sesame oil and processed (purified and/or modified) versions thereof. In a most preferred embodiment of such a parenteral feeding, the lipid carrier is (purified) olive oil.

It is another embodiment to administer modulators in such a manner that the modulator is generated in-vivo, e.g., by gene therapy and/or by local administration of enzymes (e.g., apo B glycosylation enzymes) their encoding gene(s) and/or gene fragments.

It is a further embodiment to use a method for modulating the activity of one or more elements in the complement/lipid pathway for the treatment and/or prophylaxis of diseases associated with impaired complement-mediated lipid metabolism.

It is a further embodiment to use a method for modulating the activity of one or more elements in the complement/lipid pathway for the treatment and/or prophylaxis of concomitant (infectious, autoimmune, or neoplastic) diseases that (partially) occupy the lipid eliminating complement activation pathway.

It is a further embodiment to use a method for modulating the activity of one or more elements in the complement/lipid pathway to prevent atherogenic processes of concomitant (infectious, autoimmune, or neoplastic) diseases that (partially) occupy the lipid eliminating complement activation pathway.

It is a further embodiment to use a method for modulating the activity of one or more elements in the complement/lipid pathway to efficiently manipulate the immune system.

It is a further embodiment to use a method for modulating the activity of one or more elements in the complement/lipid pathway to achieve optimum systemic immunosuppression by lipophilic immunosuppressants.

It is a further embodiment to use a method for modulating the activity of one or more elements in the complement/lipid pathway to achieve optimum oral immunization. In a preferred such embodiment, a method for modulating the activity of one or more elements in the complement/lipid pathway is used as a lymph-targeting, oro-mucosal adjuvant to induce enhanced mucosal antibody (IgA) responses, T-cell reactivity, and/or systemic T-cell and/or B-cell (IgM and/or IgG) antibody responses.

It is an embodiment to provide prophylactic measures for diseases associated with disturbances in the complement/lipid pathway by providing improved methods for diagnosing such diseases.

It is one embodiment to estimate the anti-atherogenic potential of plant-derived, synthetic, or semisynthetic substances by determining their complement activation and/or consumption activity. Complement consumption should be understood as complement entering the complement cascade thereby disappearing as free component.

It is another embodiment to estimate one or more of the complement components selected from the group comprising MBL, C4A, C4B, C2, factor B, C3adesArg, serum carboxypeptidase N, vitronectin, clusterin, and erythrocyte-bound complement receptor 1 (CR1), in blood, blood serum and/or blood plasma of a patient in order to establish the underlying or related defect of his/her atherosclerosis.

It is a further embodiment that concomitant (infectious, autoimmune, or neoplastic) diseases that may (partially) occupy the lipid eliminating complement activation pathway can be diagnosed more adequately so that atherogenic processes are prevented.

It is another aspect that an individual's lipid profile can be determined with greater accuracy by using whole blood rather than blood plasma in a lipid profile test.

It is a further embodiment to provide compositions for the treatment and/or prophylaxis of diseases associated with disturbances in the complement/lipid pathway. Compositions according to such an embodiment of the present invention may be pharmaceutical compositions, additives for pharmaceutical compositions, active substances for pharmaceutical compositions, additives for clinical nutrition and/or regular food additives and that comprise modulators according to the invention, metabolic precursors of such modulators, biochemically functional analogues, functional equivalents and/or derivatives of such modulators with or without expedients such as fillers, binders, other complement activators such as vitamin A, thickening agents, preservatives, lubricants, emulgators, and/or stabilizers.

It is an embodiment that such compositions are used to modulate the activity of one or more elements of the complement/lipid pathway according to a method of the invention.

REFERENCES

1. Ross R. The pathogenesis of atherosclerosis: a perspective for the 1990's. Nature 1993; 362: 801-809.
2. Willeit J, Kiechl S, Oberhollenzer F, Rungger G, Egger G, Bonora E, Mitterer M, Muggeo M. Distinct risk profiles of early and advanced atheroclerosis. Prospective results from the Brunneck Study. Arterioscl Thromb Vasc Biol 2000; 20: 529-537.
3. Bucher H C, Griffith L E, Guyatt G H. Systematic review on the risk and benefit of different cholesterol-lowering interventions. Arterioscl Thromb Vasc Biol 1999; 19: 187-195.
4. The Heart Outcmes prevention Evaluation Study Investigators. Effects of an angiotensin-converting-enzyme inhibitor, ramipril, on cardiovascular events in high-risk patients. N Engl J Med 2000; 342:145-53.
5. The Diabetes Control and Complication Trial Research Group. The effect of intensive treatment of diabetes on the development and progression of long-term complications in insulin-dependent diabetes mellitus. N Engl J Med 1993; 329: 977-86.
6. UK Prospective Diabetes Study (UKPDS) Group. Intensive blood-glucose control with sulphonylureas or insulin compared with conventional treatment and risk of complications in patients with type 2 diabetes (UKPDS 33). Lancet 1998; 352:837-53.
7. Haffner S M, Lehto S, Ronnemaa T, Pyorala K, Laakso M. Mortality from coronary heart disease in subjects with type 2 diabetes and in nondiabetic subjects with and without prior myocardial infarction. N Engl J Med 1998; 339: 229-34.
8. Ross R. Atherosclerosis: an inflammatory disease. N Engl J Med 1999; 340: 115-126.
9. Law S K A & K B M Reid: Complement in focus, 2nd edition, 1995. Oxford University Press, Oxford, G.B.
10. Rosenberg M E & J Silkensen: Clusterin: Physiologic and pathophysiologic considerations. Int J Biochem Cell Biol 1995; 27(7): 633-645.
11. Ishikawa Y, Akasaka Y, Ishii T, Komiyama K, Masuda S, Asuwa N, Choi-Miura N-H, Tomita M: Distribution and synthesis of apolipoprotein J in the atherosclerotic aorta. Artherioscler Thromb Vasc Biol 1998; 18:665-672.
12. Madsen H O, Videm V, Svejgaard A, Svennevig J L, Garred P: Association of mannose-binding-lectin deficiency with severe atherosclerosis. The Lancet 1998; 352: 959-960.

EXAMPLES

Example 1

Complement Components Associated with Chylomicrons

Experimental procedure: Chylomicrons were isolated from plasma by ultra centrifugation and purified by column chromatography, in the following manner: For separation of lipoproteins, plasma samples were subjected to a single ultracentrifugation step as described in detail (12). Chylomicron (Sf>1000) and non-chylomicron (Sf<1000) fractions were separated by flotation. The chylomicron fraction contained chylomicrons and large VLDL. The non-chylomicron fraction contained chylomicron remnants, small VLDL and its remnants, LDL, HDL and the remainder of the plasma proteins. Aliquots were stored at −20° C. until use. In the fractions containing large chylomicrons (large triglyceride-rich particles) complement components C3, MBL, clusterin (exp. 1), clusterin (exp. 2) and vitronectin were measured by competitive ELISA using the purified proteins and MBL- and C3-specific polyclonal and clusterin-specific monoclonal-antibodies G7* and EB-8* and vitronectin-specific monoclonal antibody MO-24* as reagents. The presence of the complement factors could consistently be demonstrated in fractions 13 through 20 (see FIGS. 4A-E). In addition, C3 and MBL were also found in other lipoproteins isolated by one-step density gradient ultra centrifugation (Redgrave gradient) (IDL, LDL, HDL) in subjects fasting and postprandial after a fat challenge.

Example 2

Adherence of Triglyceride-rich Particles to Erythrocytes in Whole Blood

Experimental procedure: To observe adherence of triglyceride-rich particles to erythrocytes in whole blood, Sudan Black staining of erythrocytes in whole blood was performed. In this procedure, blood smears were prepared and Sudan Black staining was performed with a filtered and saturated solution of Sudan Black in 80% ethanol (4 grams of Sudan Black B, Electran in 200 ml of 80% ethanol) by the following procedure. The blood film on the glass slide was fixed by heat fixation (3× through a flame). The slide was soaked in Sudan Black solution for 3 min. after which the slide was rinsed with 80% ethanol. The preparation was re-hydrated by a graded ethanol series (1 min. 40% ethanol, 1 min. 20% ethanol, 1 min. demineralized water). Excess water was shaken off and the slides were dried to air. Microscopic examination of the slides revealed that virtually all erythrocytes of healthy volunteers carried chylomicrons and chylomicron remnants 4 hours after an oral fat intake (FIG. 5A), whereas erythrocytes in the 'fasting' state carried considerably less such particles (FIG. 5B).

Example 3

Figure 6:
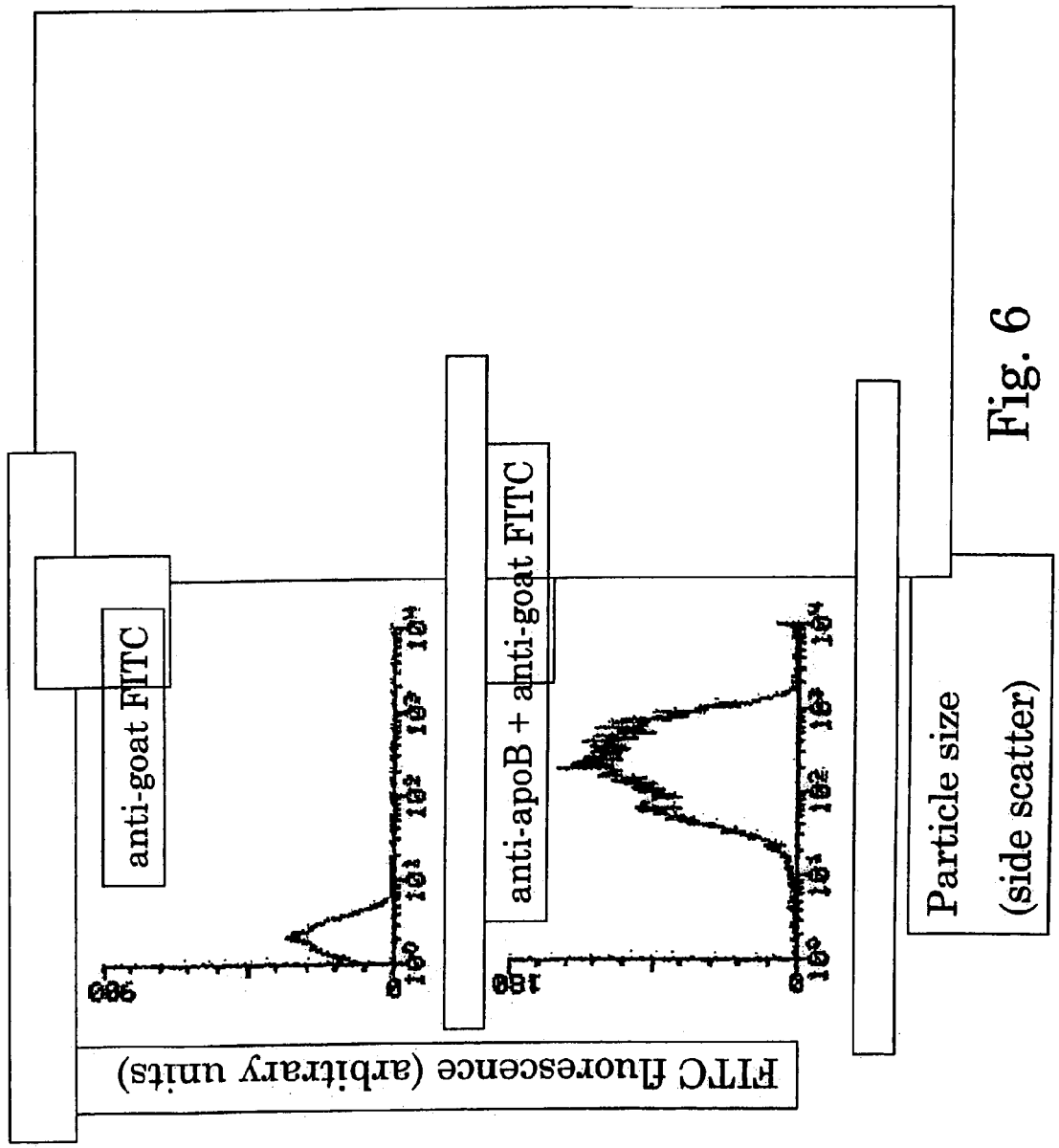
FIG. 6 shows the flow cytogram obtained after staining apo B on human erythrocytes as determined in example 3.

Measurement of Erythrocyte-bound Apo B-containing Lipoproteins by Flow Cytometry Experimental procedure: Full capillary blood was drawn from non-fasting healthy subjects by capillary function. The blood was washed 3 times in 10 ml of VSB° buffer (Veronal Saline Buffer) by centrifugation (3,000 rpm, 10 min., 20° C.) and the cell count was adjusted to $1.5 \times 10^8$/ml with VSB° buffer. A volume of 50 µl of the sample was pelleted and the pellet was re-suspended in 50 µl of a goat raised anti-human apo B polyclonal antibody solution (Chemicon 1:25 diluted in VSB° buffer). After a 30 min. incubation of the sample at room temperature (RT) the cells were washed twice in 1 ml. of VSB° buffer. The cells were pelleted and resuspended in 50 µl of a FITC-labeled anti-goat antibody solution (Rabbit anti-goat Ig FITC, DAKO 1:10 diluted in VSB° buffer). After a 30 min. incubation of the sample at RT the cells were washed twice in 1 ml. of VSB° buffer, pelleted, resuspended in 0.5 ml. of VSB° buffer and analyzed by flow cytometry (10.000 cells were counted). Erythrocytes were gated on forward and side scatter. It could be demonstrated that the FITC-label was associated with the side-scattering particles (erythrocytes) only in the presence of the anti-apo B antibodies (FIG. 6, bottom panel), whereas no erythrocytes-associated FITC fluorescence could be detected in the case that incubation with anti-apo B antibodies was omitted from the analysis (negative control sample, FIG. 6, top panel). It was therefore concluded that apo B was associated with the erythrocytes in whole blood.

Example 4

Binding and Internalization of Chylomicron Remnants by Leukocytes in the Blood (in vivo)

Figure 7:
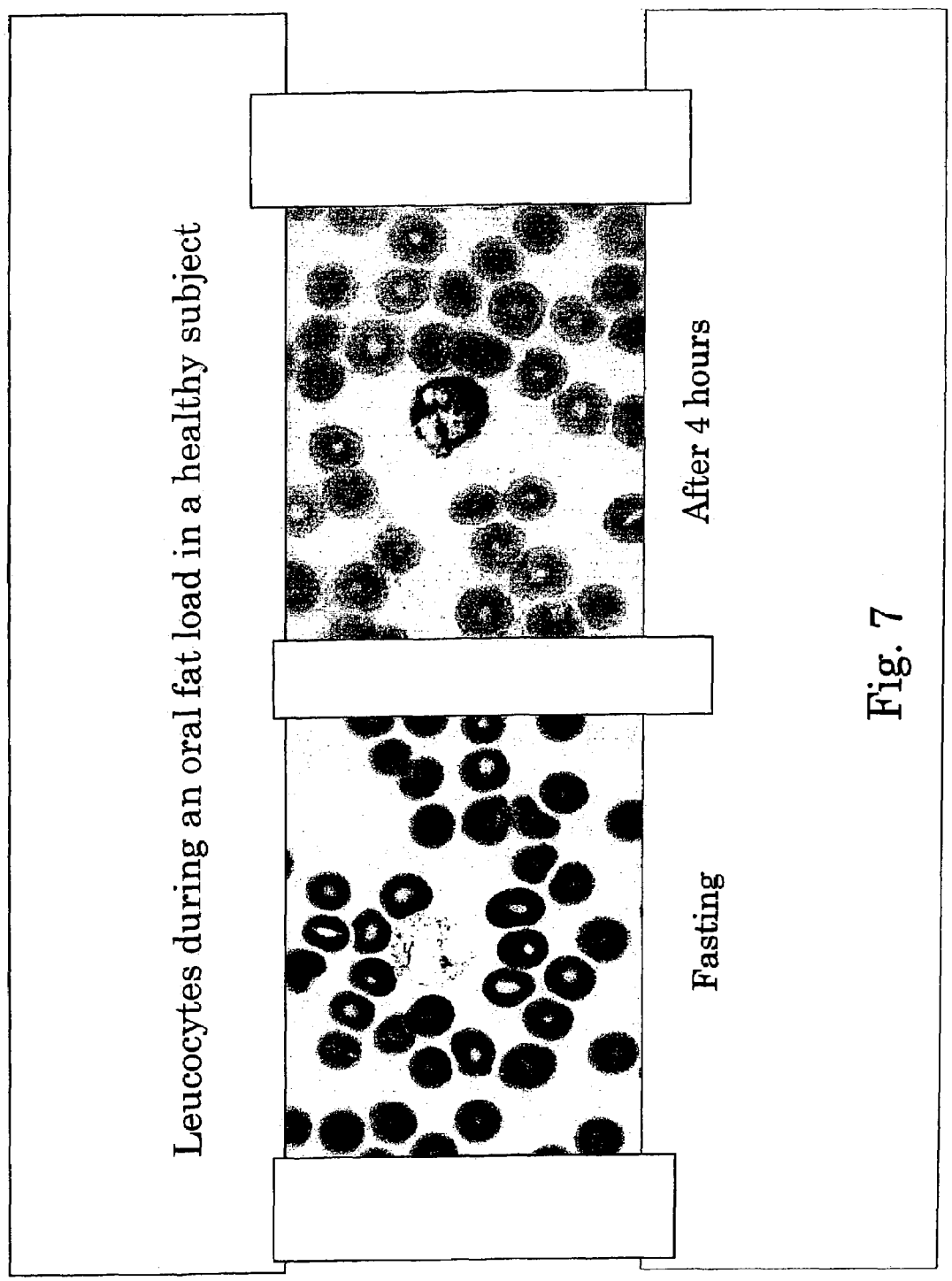
FIG. 7 shows the internalization of triglyceride-rich particles in a blood leukocyte as determined in Example 4.
Figure 8:
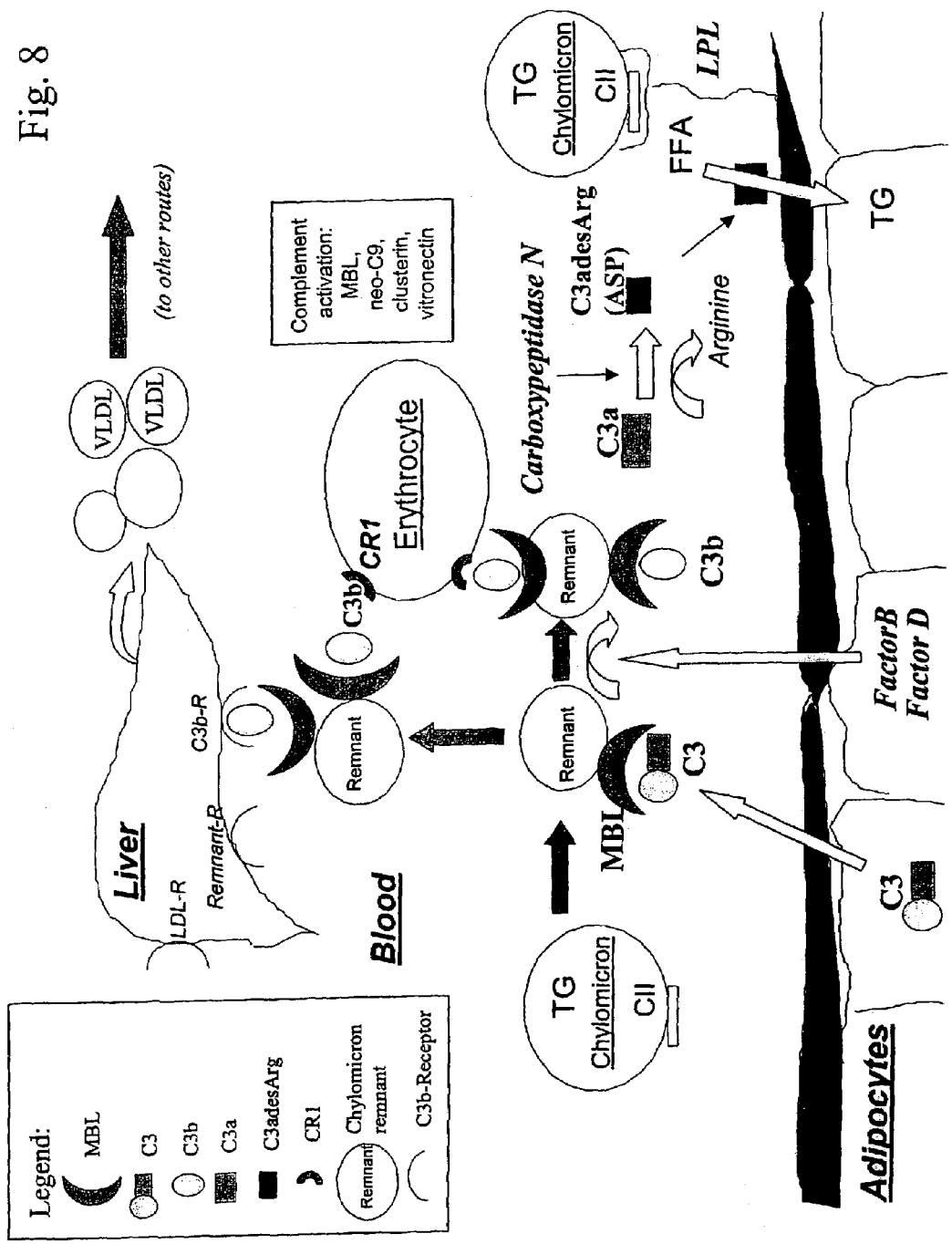
FIG. 8 shows the complement/lipid pathway in schematic representation.

Experimental procedure: Fasting venous blood was drawn and Sudan Black staining as described in example 2 was carried out (left panel of FIG. 7). In the right panel of FIG. 7, venous blood of the same healthy volunteer was drawn 4 hours after administration of a standardized oral fat load. In the oral RP-fat loading test, cream is used as fat source; this is a 40% (w/v) fat emulsion with a P/S ratio of 0.06, which contains 0.001% (w/v) cholesterol and 2.8% (w/v) carbohydrates. After an overnight fast of 12 h, the subjects ingest the fresh cream, to which 120.000 U of aqueous RP (Retinyl palmitate=vitamin A) had been added 18 h before the test, in a dose of 50 g per $m^2$ body surface. After the ingestion of the fat load, subjects were only allowed to drink water or tea during the following 24 h. Peripheral blood samples were obtained in sodium EDTA (2 mg/ml) before (T=0), at hourly intervals up to 10 h and at 12 and 24 h after the meal. Tubes were protected against light by aluminum foil and centrifuged immediately for 15 min at 800×g at 4° C. Blood samples for FFA measurement were chilled and a lipase inhibitor (Orlistat) was added in order to block in vitro lipolysis.

Increased leukocyte concentrations in the postprandial situation are involved in the process of atherosclerosis (novel finding by our own group).

After having taken up surface fragments from triglyceride-rich particles or whole remnant particles, neutrophilic granulocytes become activated and induce a pro-inflammatory response which is the first step in the generation of atherosclerosis and endothelial damage.

Example 5

Magnitude and Time-dependency of Increase of Complement Component 3 (C3) in the Postprandial Period Experimental procedure: Standardized oral fat loading tests (oral RP fat loading test) were performed in volunteers and patients and plasma C3 levels were determined nephelometrically at regular intervals. Complement component 3 was measured by nephelometry (Dade Behring Nephelometry type II). Maximal postprandial C3 concentrations were in most cases found after 2 hrs. (data not shown). This is consistent with the concept of chylomicron-driven complement activation (MBL mediated) followed by a compensatory C3 synthesis in vivo. We therefore conclude that complement activation occurs in vivo during postprandial lipemia (high blood lipid concentrations).

Example 6

Binding and Internalization of Chylomicron Remnants by Leukocytes in the Blood (in vitro)

Experimental procedure: In vitro incubations of chylomicron remnants with isolated human leukocytes were performed by methods described in example 3. Internalization of remnants in leukocytes was observed (data not shown).

Example 7

Assay for Complement-activation Cq. Complement-consumption by Drugs/Food Components Intended for Application in Atherosclerosis or Clinical Nutrition Experimental procedure: In microtiter plates, one "classical" pathway unit of serum or one "alternative" pathway unit of serum was incubated for 0.5 hrs. with a dilution series of the substance to be investigated. In order to do so, the substance of interest is suspended in micellar form. After incubation, residual classical and alternative complement activities are estimated by conventional techniques (Klerx J P A M, Beukelman C J, Van Dijk H and Willers J M N (1983) J. Immunol. Lett. 63:215-220; Van Dijk H, Rademaker P M and Willers J M N (1985) J. Immunol. Meth. 85: 233-244). The degree of complement consumption is a measure of complement activation by the components. A large number of compounds were identified by this in vitro assay for application in atherosclerosis or clinical nutrition.

Example 8

MBL-dependent Complement Activation by Chylomicrons in Human Serum

Experimental procedure: Chylomicrons were isolated from human serum by ultra centrifugation and purified by column chromatography. The purified chylomicron fractions were added to MBL-positive serum (from healthy human subjects) and MBL-negative serum (from MBL-deficient human subjects) and purified heterologous chicken erythrocytes were added. Complement activation was allowed to occur at 37° C. for 45 min. after which the extent of hemolysis was evaluated by spectrophotometrical determination of hemoglobin levels in serum supernatants. It was found that hemolysis of heterologous erythrocytes was extensive in the case that an MBL-positive serum was used, whereas hemolysis was virtually absent in the case of an MBL-negative serum (data not shown). This demonstrated that chylomicrons can bring about complement activation in human serum in an MBL-dependent manner.

Figure 9:
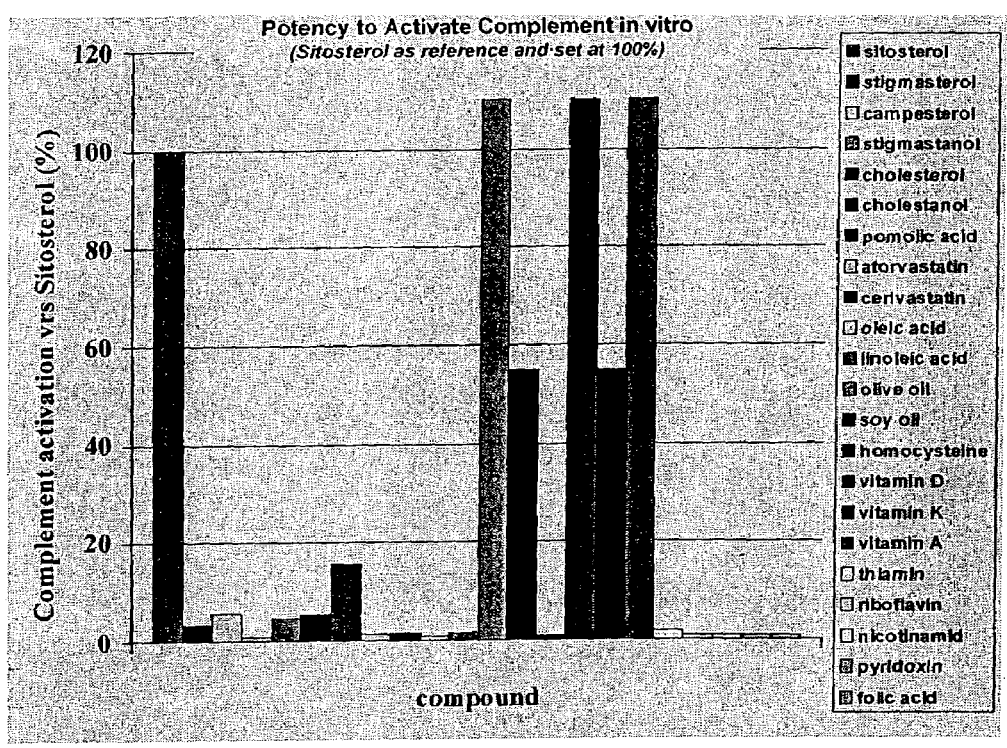
FIG. 9 shows the potency of different substances to activate complement in vitro.

Using the MBL in-vitro assay, we identified the components from olive oil and soy oil inducing Complement Lipid Pathway (CLiP)-activation. The results are summarized in FIG. 9.

From these results, two compounds were selected which show strong CLiP-induction and which are known to be safe to be administered to human (thanks to other clinical use), specifically (i) glycosylated plant sterols and (ii) vitamin A.

Example 9

Postprandial C3 Buildup

Experimental procedure: Full capillary blood was draw from healthy subjects and the C3 levels were determined together with the leukocyte count. Postprandial (situation in blood after a meal) leukocyte increase and activation was associated with postprandial complement C3 increase. In the early postprandial phase (<4 hr) predominantly neutrophilic granulocytes were observed, whereas between 4 and 10 hrs into the postprandial period, an increase of lymphocytes was observed. These findings were consistent with the notion that leukocytes play a role in atherosclerosis by the formation of foam cells.

Example 10

Effect of Glycosylated Plant Sterols on Fasting Plasma Triglycerides and Cholesterol Levels in Two MBL-deficient Patients and in One MBL-normal Patient with Heterozygous Familial Hypercholesterolemia Proof of principle has been reached in 2 MBL-deficient patients.

These subjects were treated with a diet enriched in glycosylated plant sterols during 3 weeks. The glycosylated plant sterols were selected in the MBL in vitro test as described in example 8. This intervention resulted in a decrease of fasting plasma triglycerides and cholesterol (Table 1)

TABLE 1

Effect of glycosylated plant sterols on blood parameters of MBL-deficient patients.

| | Plasma TG (mM) | | Cholesterol (mM) | | apoB (g/L) | |
|---|---|---|---|---|---|---|
| | Before | After | Before | After | Before | After |
| MBL def1 | 3,66 | 2,27 | 4,8 | 4,2 | 0,85 | 0,89 |
| MBL def2 | 0,88 | 0,79 | 4,8 | 3,6 | 0,62 | 0,56 |

Figure 10:
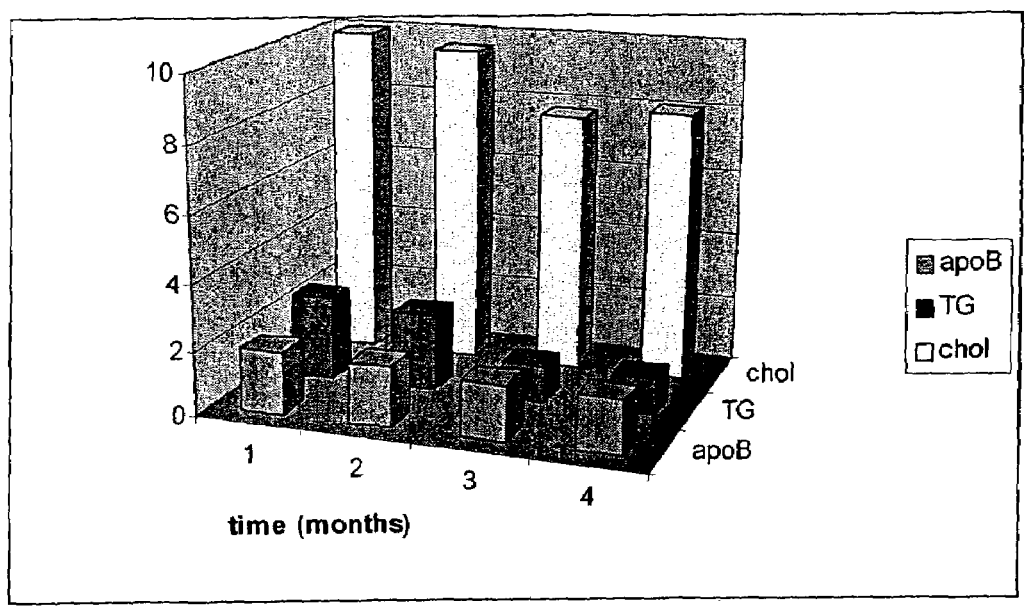
FIG. 10 shows the effects of glycosylated plant stanols on fasting triglycerides, plasma apoB and plasma cholesterol levels over a four month period in a patient with heterozygous Familial Hypercholesterolemia.

Using a different intervention with glycosylated plant stanols in a patient with heterozygous Familial Hypercholesterolemia (with relatively normal MBL activity in plasma), refractory to therapy with expanded dose statins in combination with a lipid lowering diet and resins, significant reductions of plasma cholesterol (from 10 to 7.8 mmol/L), fasting plasma triglycerides (from 2.3 to 1.08 mmol/L) and plasma apoB (from 1.90 tot 1.62 g/L) were achieved reaching the lowest concentration ever experienced by this patient (FIG. 10). This example provides in vivo support for the Complement Lipid Pathway (CLiP) concept developed by C-Tres, using a sub-optimal lead.

Example 11

Effect of Vitamin A on Post-prandial CLiP Stimulation

Figure 11A:
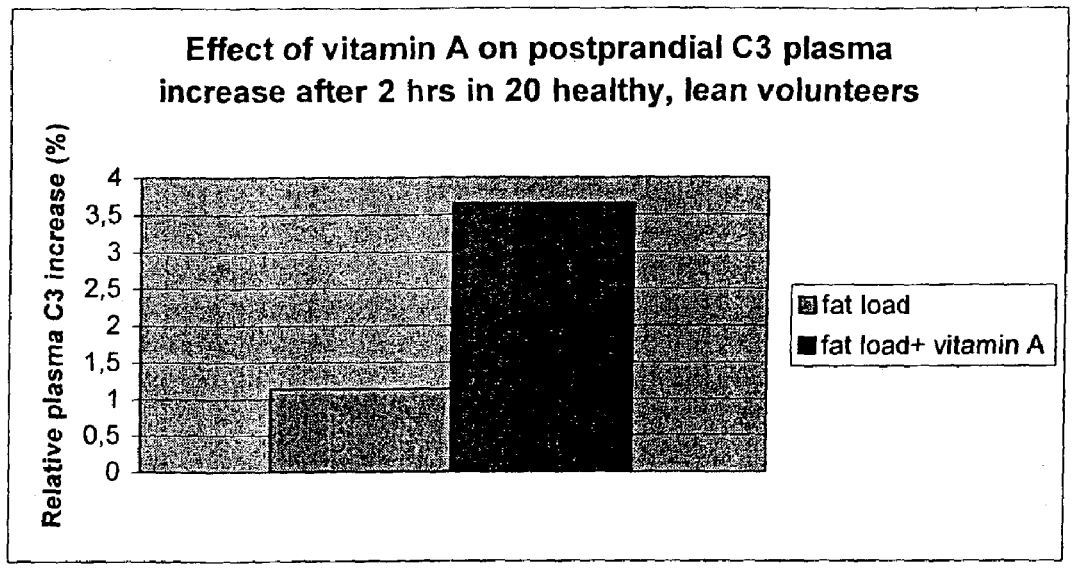
FIG. 11a shows the effect of vitamin A on postprandial C3 plasma concentration after 2 h in healthy lean volunteers.

Another series of lead compounds, namely vitamin A-analogues, were tested in 20 healthy volunteers in order to determine the CLiP stimulating potency of these leads that had shown CLiP stimulation in vitro (Example 8). Twenty healthy volunteers were tested on two different occasions. Blood was drawn before and after ingestion of a standardized oral fat load with and without vitamin A (as representative for these series of leads) given to the participants in random order. Addition of vitamin A to the oral fat load resulted in a significantly higher postprandial plasma C3 increase, whereas the same amount of fat was ingested in both situations (FIG. 11a).

Figure 11B:
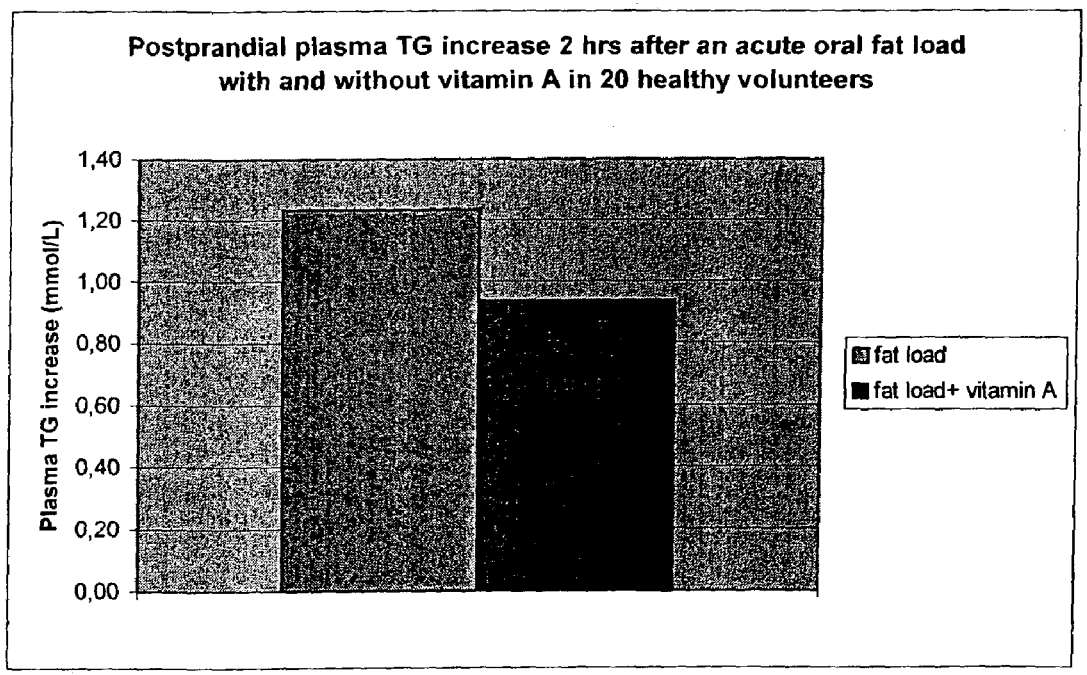
FIG. 11b shows the effect of vitamin A on postprandial plasma triglyceride concentration after 2 h in healthy lean volunteers.

The levels of plasma trygliceride increase 2 h after acute oral fat load also showed a reduction in the volunteers if the fat load was given with vitamin A (FIG. 11b)

This is in line with the CLiP concept that by activating the Complement system, plasma triglycerides will be reduced even in healthy normolipidemic subjects. Note: it should be stressed that the C3 increase in this group of young, healthy, lean subjects was expected to be lower due to the characteristics of the subjects. In older, insulin-insensitive subjects the postprandial C3 response is much higher.

These experiments in human gave the expected results upon administration: increase of C3-titers and decrease of triglycerides. It is therefore reasonable to assume that also other compounds, active in the in vitro assay, show CLiP-activities in human.

Other Analytical Methods:

Triglyceride-rich particles in plasma, chylomicrons and non-chylomicrons were determined by HPLC as described (14). TG and cholesterol were measured in duplicate by commercial calorimetric assay (GPO-PAP, and Monotest Cholesterol kit, Boehringer Mannheim) as described (14, 23). Plasma apo B and apo A1 were determined by immunoturbidimetry (23). Apo E genotype was determined as described (47-49). HDL2 and HDL3 cholesterol concentrations were determined by precipitation procedures as described (50). Complement factor 3 was measured immunoturbidimetry or nephelometrically. Acylation stimulating protein was determined by ELISA, as were factor B and D. Ketone bodies were measured by HPLC.

What is claimed is:

1. A method for determining the anti-atherogenic potential of a potential enhancer of the complement/lipid pathway, said method comprising:
    carrying out an in vitro assay in which complement activation activity and/or complement consumption activity of said potential enhancer in the complement/lipid pathway is detected so as to determine the potential enhancer's anti-atherogenic potential;
    wherein the presence of complement activation activity and/or complement consumption activity of the potential enhancer indicates that the potential enhancer has anti-atherogenic potential.

2. The method according to claim 1, wherein said in vitro assay comprises flow cytometry of a cell surface complex of complement components.

3. The method according to claim 1, wherein the potential enhancer is selected from the group of vitamin A, glycosylated plant sterols, glycosylated plant stanols, mannose binding lectin ("MBL") and MBL-replacement factors.

* * * * *